(12) United States Patent
McCoy

(10) Patent No.: US 7,826,726 B2
(45) Date of Patent: Nov. 2, 2010

(54) INTRA-CONVERTIBLE THERMAL VAPOR EXTRACTION AND DELIVERY SYSTEM

(76) Inventor: Mark S. McCoy, 969-G Edgewater Blvd., #229, Foster City, CA (US) 94404

( * ) Notice: Subject to any disclaimer, the term of this patent is extended or adjusted under 35 U.S.C. 154(b) by 1047 days.

(21) Appl. No.: 11/146,931

(22) Filed: Jun. 6, 2005

(65) Prior Publication Data

US 2005/0279353 A1    Dec. 22, 2005

Related U.S. Application Data

(60) Provisional application No. 60/577,799, filed on Jun. 7, 2004.

(51) Int. Cl.
*F24C 7/00* (2006.01)

(52) U.S. Cl. .................. 392/407; 392/409; 128/200.24

(58) Field of Classification Search .................. None
See application file for complete search history.

(56) References Cited

U.S. PATENT DOCUMENTS

| | | |
|---|---|---|
| 649,521 A | 5/1900 | Libbey |
| 719,683 A | 2/1903 | Moehlenbrock |
| 933,360 A | 9/1909 | Carabias |
| 972,737 A | 10/1910 | Tobias |
| 1,313,280 A | 8/1919 | Falkenau |
| 1,357,601 A | 11/1920 | Walter |
| 1,957,143 A | 5/1934 | Kretzner |
| 2,129,129 A | 9/1938 | Groulx |
| 2,360,628 A | 10/1944 | Wright |
| 3,079,928 A | 3/1963 | Jensen |
| 3,115,134 A | 12/1963 | Schmahl |
| 3,750,677 A | 8/1973 | Jodoin |
| 3,863,647 A | 2/1975 | Unger |
| 3,949,743 A | 4/1976 | Shanbrom |
| 4,083,374 A | 4/1978 | Jacobsen |
| 4,141,369 A * | 2/1979 | Burruss ...................... 131/330 |
| 4,224,953 A | 9/1980 | Alvarez |
| 4,303,083 A * | 12/1981 | Burruss, Jr. .................. 131/271 |
| 4,474,191 A * | 10/1984 | Steiner ..................... 131/198.2 |
| 4,637,407 A * | 1/1987 | Bonanno et al. ............. 131/175 |
| 4,735,217 A * | 4/1988 | Gerth et al. .................. 131/273 |

(Continued)

FOREIGN PATENT DOCUMENTS

DE    195 41 690 A1    10/1996

(Continued)

*Primary Examiner*—Thor S Campbell
(74) *Attorney, Agent, or Firm*—Lewis and Roca LLP

(57) ABSTRACT

An intra-convertible thermal vapor extraction and delivery system comprising: an ergonomically-shaped casing comprising a heating element, a fan, an output nozzle thermally coupled to the heating element and having a nozzle base and a tapered nozzle end, and a nozzle sleeve; and a cradle having a bottom surface and a top surface, wherein bottom surface is substantially planar, and top surface is substantially concave so as to accept and securely hold the casing, wherein the fan is positioned substantially behind the heating element so as to blow ambient air through the element, heating it to a desired temperature, and forcing it through the output nozzle, and wherein the nozzle base is positioned to receive the air before the tapered nozzle end, and the nozzle base has a greater outer diameter than the tapered nozzle end, creating a step at the transition between the nozzle base and the tapered nozzle end.

18 Claims, 25 Drawing Sheets

U.S. PATENT DOCUMENTS

| | | | |
|---|---|---|---|
| 4,807,646 A | 2/1989 | Sahar | |
| 4,922,931 A | 5/1990 | Nare et al. | |
| 4,967,742 A | 11/1990 | Theodorou | |
| 5,086,766 A | 2/1992 | Beacham | |
| 5,195,164 A * | 3/1993 | Lambert | 392/385 |
| 5,331,979 A * | 7/1994 | Henley | 131/273 |
| 5,558,084 A | 9/1996 | Daniell et al. | |
| 5,564,442 A * | 10/1996 | MacDonald et al. | 131/194 |
| 5,598,835 A | 2/1997 | von Schrader | |
| 5,613,489 A | 3/1997 | Miller et al. | |
| 5,638,833 A * | 6/1997 | Bowen et al. | 131/202 |
| 5,750,964 A * | 5/1998 | Counts et al. | 219/535 |
| 5,857,263 A * | 1/1999 | Chan | 34/97 |
| 5,993,748 A | 11/1999 | Wheeler | |
| RE36,995 E * | 12/2000 | Andis | 34/97 |
| 6,250,301 B1 * | 6/2001 | Pate | 128/203.26 |
| 6,354,301 B2 * | 3/2002 | McCoy | 131/194 |
| 6,481,437 B1 * | 11/2002 | Pate | 128/203.26 |
| 6,513,524 B1 | 2/2003 | Storz | |
| 6,715,494 B1 * | 4/2004 | McCoy | 131/194 |
| 6,738,564 B1 * | 5/2004 | Tung | 392/385 |
| 6,772,756 B2 * | 8/2004 | Shayan | 128/203.26 |
| 6,925,729 B2 * | 8/2005 | Sullivan et al. | 34/97 |
| 6,928,235 B2 * | 8/2005 | Pollack | 392/380 |
| 7,069,073 B2 * | 6/2006 | Henley et al. | 604/20 |
| 7,077,370 B2 * | 7/2006 | Lin et al. | 248/176.2 |
| 7,445,007 B2 * | 11/2008 | Balch et al. | 128/203.27 |
| 7,458,374 B2 * | 12/2008 | Hale et al. | 128/203.26 |
| 2001/0039953 A1 * | 11/2001 | McCoy | 131/229 |
| 2002/0006275 A1 * | 1/2002 | Pollack | 392/380 |
| 2005/0279353 A1 * | 12/2005 | McCoy | 128/200.24 |
| 2005/0282100 A1 * | 12/2005 | Lin | 431/268 |
| 2007/0280652 A1 * | 12/2007 | Williams | 392/386 |

FOREIGN PATENT DOCUMENTS

| | | |
|---|---|---|
| DE | 195 41 528 A1 | 5/1997 |
| DE | 296 10 936 U1 | 5/1997 |

* cited by examiner

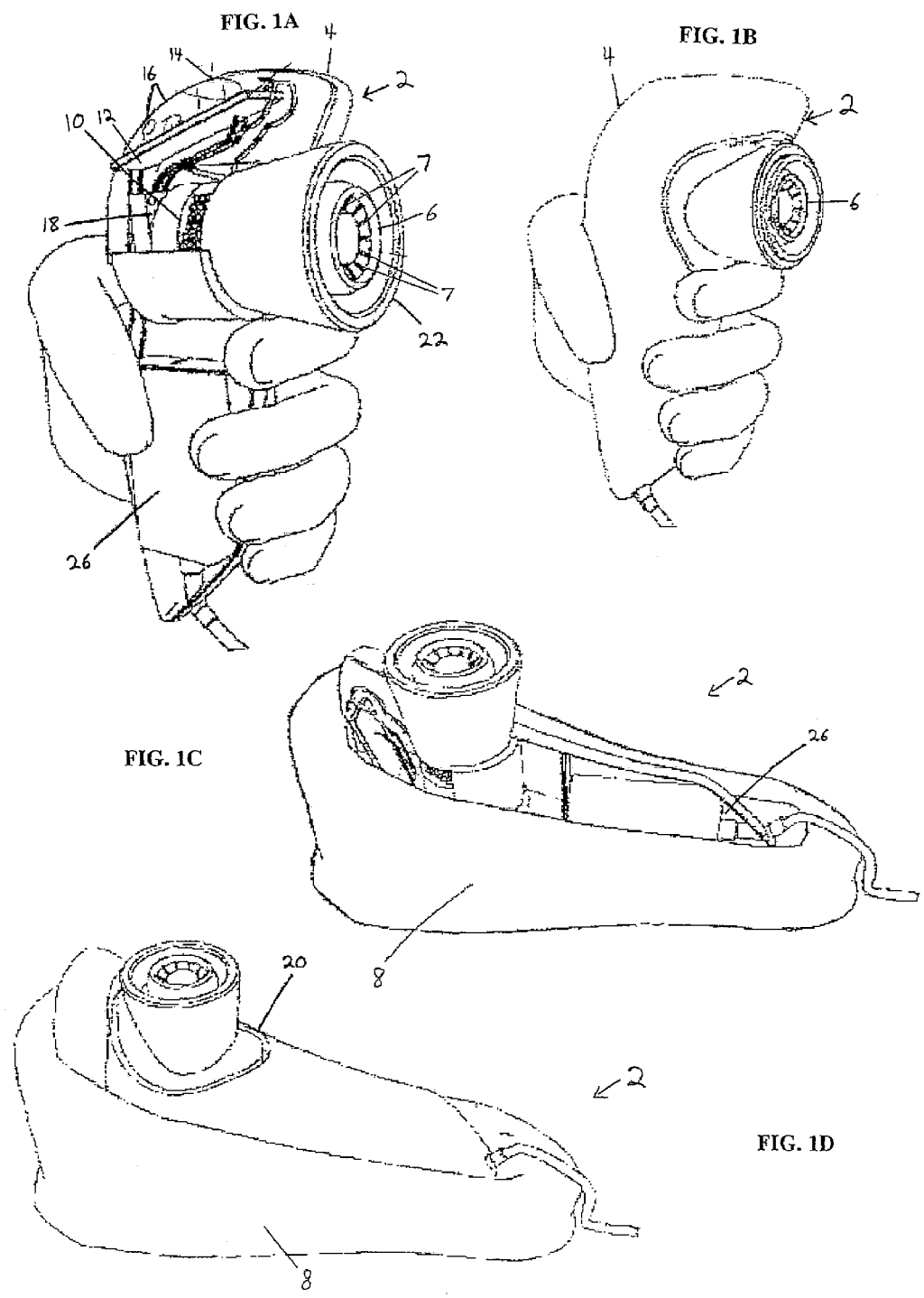

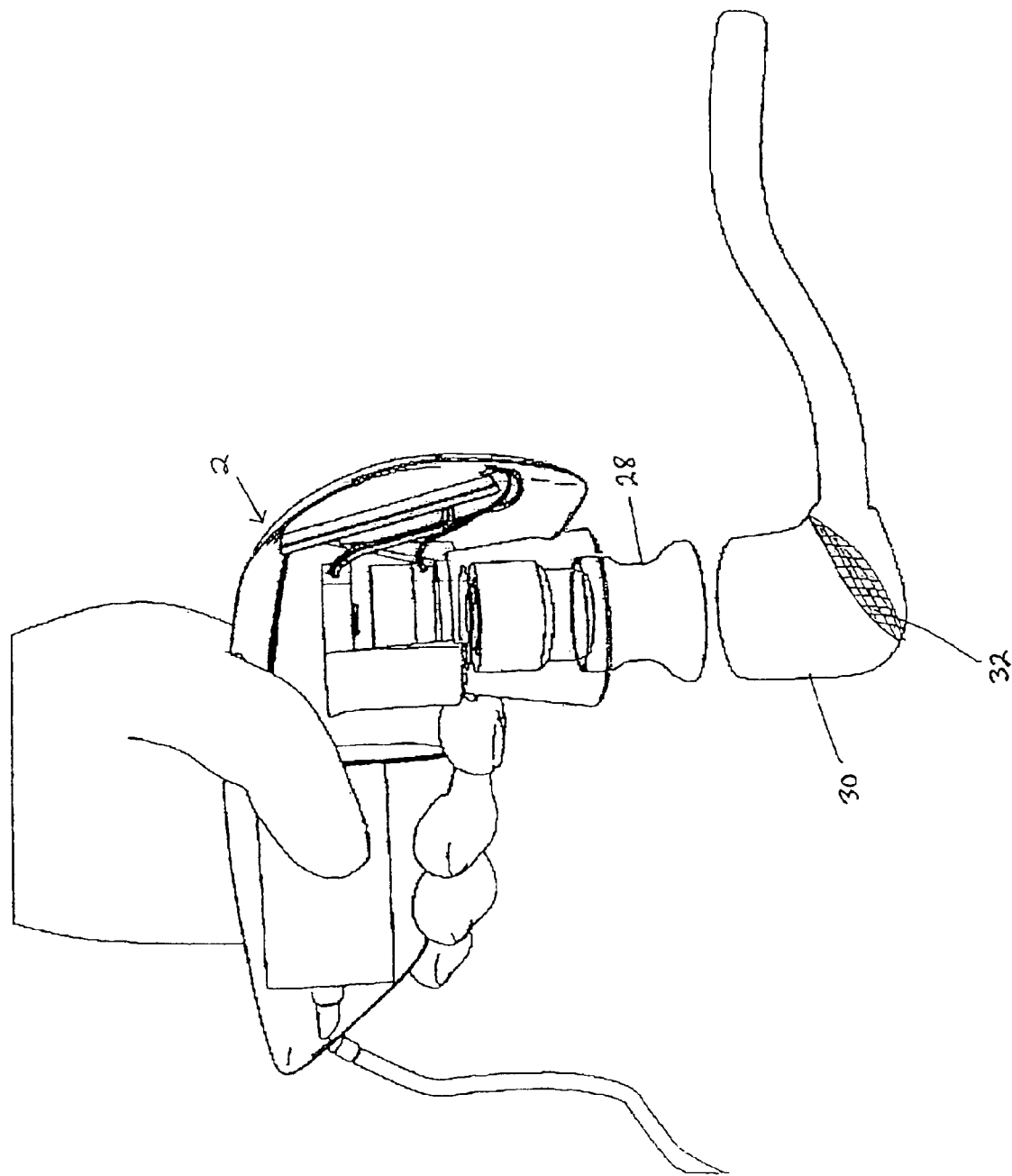

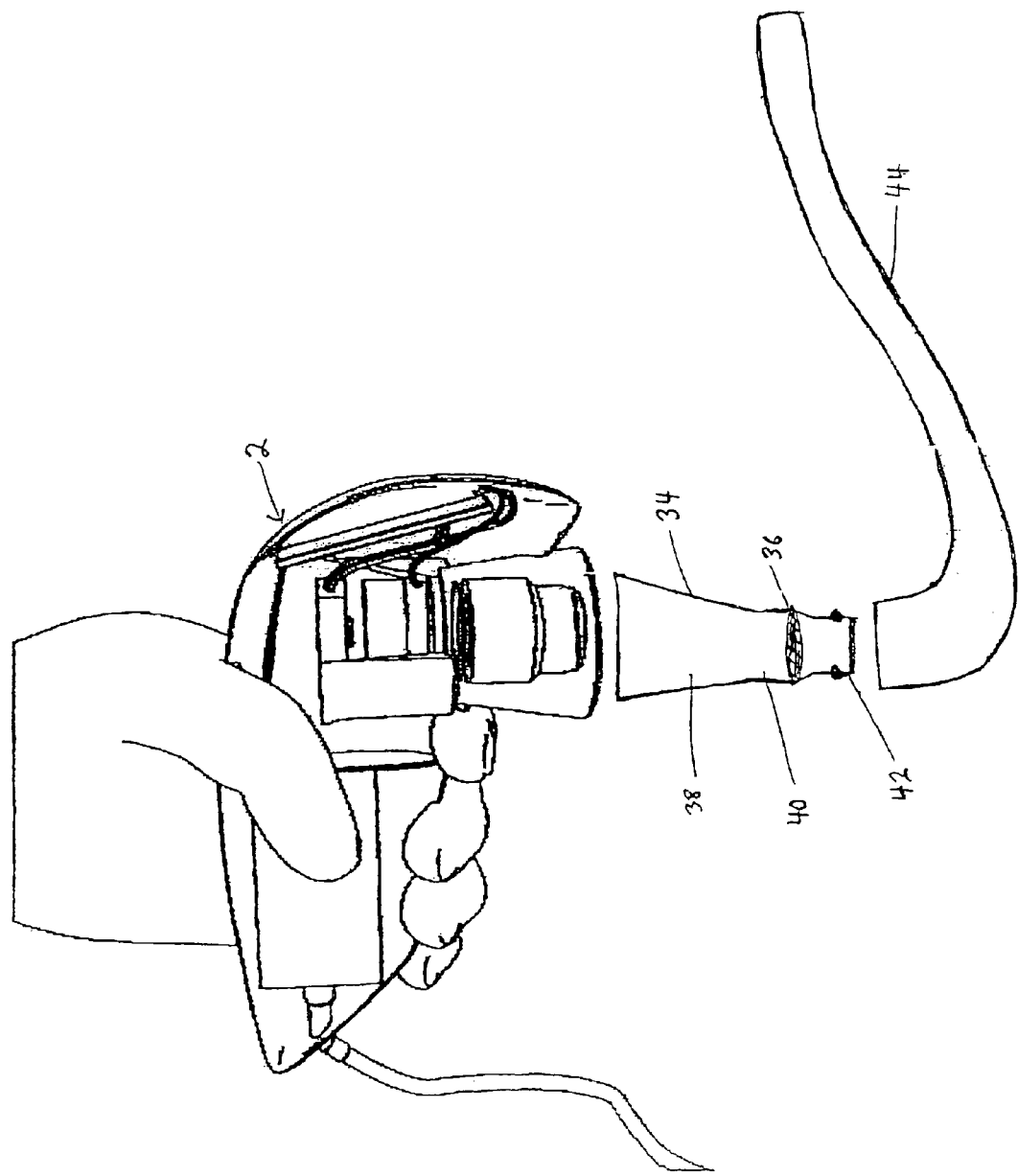

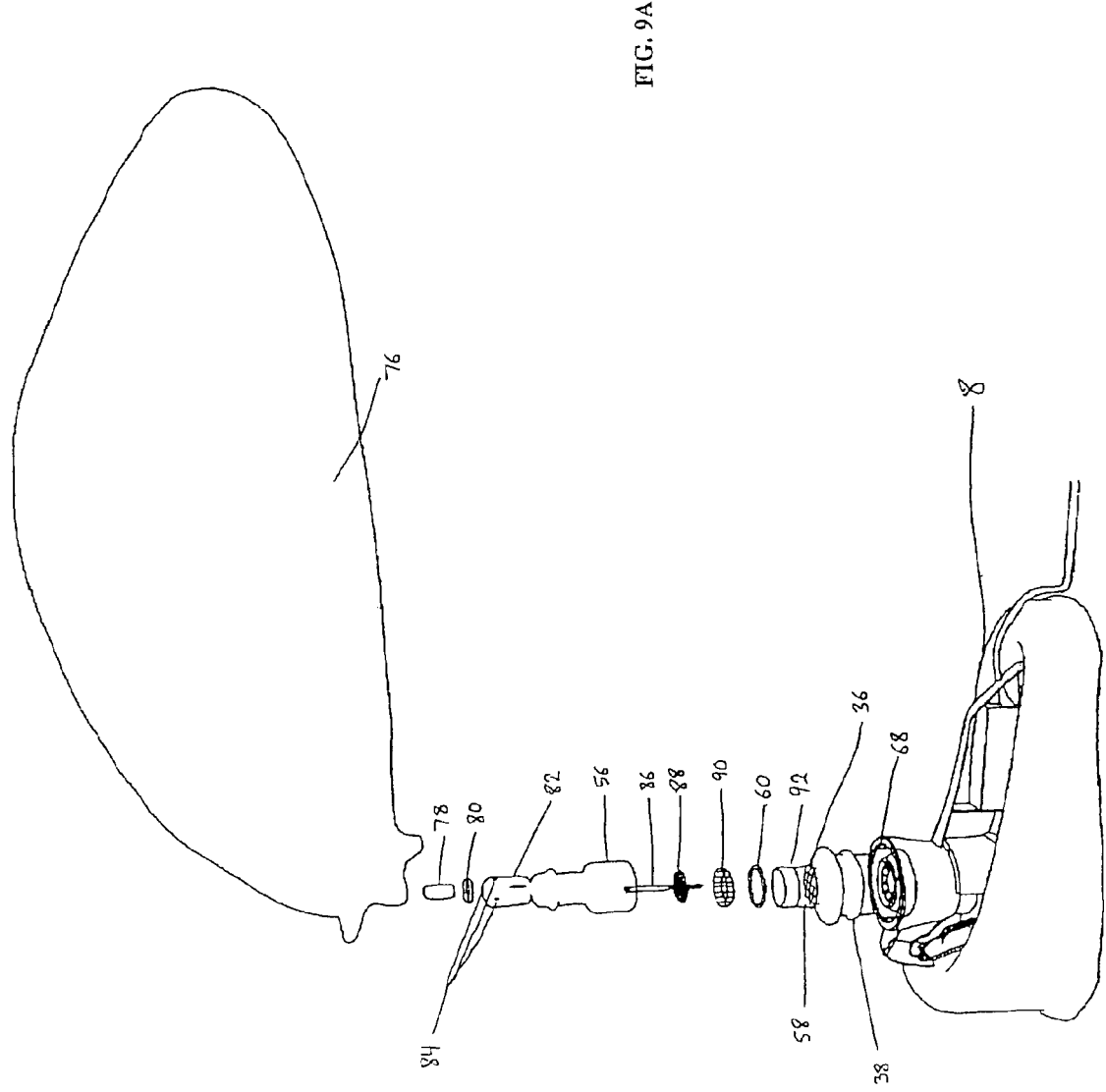

INTRA-CONVERTIBLE THERMAL VAPOR EXTRACTION AND DELIVERY SYSTEM

CROSS-REFERENCE TO RELATED APPLICATIONS

This application claims priority to U.S. Provisional Application Ser. No. 60/577,799, filed Jun. 7, 2004, which is hereby incorporated by reference as if set forth herein.

BACKGROUND

1. Field of the Invention

The present invention relates to various thermal-based devices, systems, and methods used for smoking harm reduction and for the practice of Hot Gas Extraction Aromatherapy and Medical or Phyto-Inhalation, in which heat is used to extract aromatic and/or physiologically active compounds from plants, botanicals, or orthomolecular compounds as a vapor for the purpose of vapor delivery via environmental diffusion and inhalation, direct or indirect vapor inhalation, or the collection of extracted vapor or vapor condensate for subsequent use (i.e. for the production of oil, tincture, or tea concentrates). The present invention contains elements of novel design and original conception and also seeks to improve upon and expand the usefulness of prior art in the field.

2. The Prior Art

At the present time, aromatic and active compound containing vapors are extracted and delivered primarily by one of six different approaches:

1) By extracting the aromatic and active compounds using a solvent and then atomizing this mixture into a vapor or mist that can be inhaled;
2) By extracting the aromatic and active compounds using a solvent and then heating this mixture until a vapor is formed and diffusing it into the ambient atmosphere;
3) By combustion smoking or smoldering of various plant and botanical materials or concentrates (previously extracted oils and resins), whereas the smoke produced contains a small amount of the aromatic and active compounds in vapor form which is inhaled simultaneously with the smoke;
4) By conductive vaporization where a hot surface is used to heat the substrate until the vapors release and then are either inhaled directly or captured for subsequent delivery;
5) By convective vaporization using a heating element with or without a thermo-coupled controller or fan mated to an extraction chamber holding the extract to extract the vapor that is then either inhaled directly or captured for subsequent delivery. Some of these systems use an industrial heat gun that is not accurate enough for a medical level of accuracy and is not FDA compliant, but works well nonetheless as the heat source; or
6) By a combination of convective and conductive extraction and indirect or direct inhalation.

The disadvantages of current approaches include: complexity and hassle of solvent extraction and the chemical nature of the solvents themselves which are often a trigger for allergies; "vapor cigarettes" that still deliver harmful amounts of smoke; heat guns currently used are too big and bulky and not accurate enough or FDA compliant; some systems have metal extraction chambers or metal hot plates that are incapable of maintaining a stable temperature and sometimes release metal ions that affect the aromatics; many of the systems are dry delivery which will irritate the throat; many of the systems are far two slow to warm up and too slow in the extraction; many of the systems capture the vapor prior to delivery and expose it to air that leads to uncontrolled oxidation; smoking, the most common approach, is known to be harmful to cardio vascular health because smoke contains a whole array of undesirable components such as noxious gases and known carcinogenic compounds and so is contra-indicated for therapeutic applications.

Most of the newer art belongs in one of the two last aforementioned categories. It represents the current cutting edge of the products available in the marketplace and, as such, is fairly well tested at this time. The actual field-testing of the currently available products represented in the prior art clearly demonstrates a number of disadvantages not yet addressed. The present invention aims to improve upon the prior art with one or more of the possible configurations represented.

Jenson (U.S. Pat. No. 3,079,928) discloses one such smoking apparatus that is very representative of the basic structures of many commonly used designs. Jenson's smoking pipe primarily consists of a mouthpiece, a removable bowl, and a stem. The bowl is attached or detached through the use of simple threads. With the bowl in place, just as Jenson discloses, the intra-convertible heat tool of the present invention can be used in hand-held mode by simply aiming the hot air output at the substrate contained in the bowl, so that it can be heated rather than incinerated and the user can inhale aromatic vapor instead of smoke. The efficiency of this approach could be further improved by using the intra-convertible heat tool with the addition of a tapered nozzle attachment to improve the mating of the heat tool to the pipe bowl, and thus, improve the efficiency of the vapor extraction.

Jenson discloses the removable bowl feature as intended for the purpose of ease of cleaning. The feature has obviously been found to be quite useful as it has been adapted broadly by others in the same field. However, such a feature also serves to make this common design modifiable for further improvement in vapor extraction efficiency with the addition of either a one piece or a two piece extraction chamber having a sequential venturi-inducing intake and lower chamber designs that mate to the intra-convertible heat tool of the present invention in place of the standard bowl as disclosed.

As with all other prior art smoking pipe apparatuses, Jenson's design is intended for combustion smoking. The tobacco, or other herb, is intended to be placed within the open bowl portion of the apparatus where it is ignited by a source of ignition, such as a lighter or match, and allowed to incinerate or burn while the smoker periodically draws, or inhales, the smoke. Medical research has deemed smoking to deliver not only a very small amount of the aromatic oils found in the tobacco or other herbs, but a whole host of particulate matter, tars, and noxious gases now proven scientifically to be hazardous to the user's health and often cancerous. The present invention is intended to expand the usefulness of and/or modify apparatuses, such as disclosed by Jenson, to preserve much of the process or ritual associated with it's conventional use, but to also enable the delivery of aromatic oil vapor void of such harmful components in lieu of smoke.

The present invention is also intended to offer a more efficient, appealing, and/or cost effective alternative to complete single-usage mode vaporization systems such as the Vaporizer For Inhalation And Method for Extraction of Active Ingredients From a Crude Natural Product or other Matrix disclosed by Pate (U.S. Pat. No. 6,250,301), the Hot Gas Extraction Device For Volatizing At Least One Substituent Of A Material disclosed by Wheeler (U.S. Pat. No. 5,993, 748), or the Inhaler For Production Of Aroma- and/or Active Substance Containing Vapors of Plant Materials and/or Fluids disclosed by Storz (U.S. Pat. No. 6,513,524).

Pate discloses a complete vapor extraction system consisting of a hot air source, such as a hot air gun or a high pressure tank with heat exchanger, that introduces hot air from below. The hot air then ascends through a permeable support structure (e.g. fritted glass disk, etc.), subsequently causing specimen particles disposed on the permeable support structure to be suspended within the confines of an isolations chamber, which is said to allow maximized gas extraction exposure for each suspended particle, and promote a uniform extraction of the aggregate charge through it's periodic mixing. Pate goes on to further disclose a filter for preventing the particles from being inhaled by the user and an embodiment that includes a side arm that can be used to divert mixed purge gases from the specimen required to be under inert gas during its extraction for the purpose of preventing wasteful loss of active ingredients.

Since Pate's system relies on either a hot air gun that is big, bulky, non-ergonomic, and not FDA compliant, or a high pressure tank with heat exchanger that is cost prohibitive, even larger and bulkier, and would only reasonably be viable in a laboratory environment for the heated gas source, the present invention offers distinct advantages over Pate. Most notably the present invention offers a use-specific, more ergonomic heat source that uses medical grade rather than industrial grade components. The heat source of the present invention is also FDA compliant and intra-convertibly compatible with other systems, offering more usage options without the added expense of additional heat sources.

Pate does not disclose an embodiment that enables extraction efficiency optimization via Venturi or turbulence creating members prior to or within the extraction chamber. Pate also fails to offer an embodiment that enables moisture conditioning of the vapor. These elements exist in one ore more of the present invention's configurations and represent a clear and substantial improvement over the prior art. In the present invention's secondary form, using a thermo-coupled hot air gun as the heat source with the same range of compatibility, the intra-convertible nature, the extraction efficiency optimization elements of the various extraction apparatuses provided for, and the moisture conditioning delivery vessel capabilities all contribute to a clear and substantial improvement over the prior art as disclosed by Pate.

Wheeler discloses a complete system comprised of a bowl-like container for holding the material from which vapor is to be extracted. It has an open end and an opposing discharge conduit, a heating tool that consists of a cap with holes in it that houses a heating element and that seals atop the open end of the bowl-like container, and a vapor collection vessel of sorts that the vapor is intended to be collected and cooled in that communicates with a user intake tube that would allow the user to draw off the extracted vapor for inhalation. Like other vaporization delivery mediums currently available, Wheeler's device relies on the systematic combination of all components to function as such, and none of the components are intra-convertible or cross-compatible with any other vapor extraction and delivery system. Additionally, like other vaporization delivery mediums currently available, it consists of a vessel that collects the vapor prior to inhalation, undesirably exposing it to substantial air volume that can lead to uncontrolled oxidation of the therapeutic components in the vapor.

The present invention, in one or more of its configurations, is intended to enable the hot gas extraction vaporization function in much the same way as Wheeler's device, but improved through the use of a use-specific, more ergonomic heat source that uses medical grade rather than industrial grade components, is FDA compliant, and is intra-convertibly compatible with multiple vapor extraction and delivery systems, offering more usage options without the added expense of additional heat sources. It also delivers the vapor in one or more configurations with minimal exposure to air volume in order to prevent uncontrolled oxidation.

Wheeler does provide for a Venturi-inducing reduction in the diameter of the extraction chamber after the convective hot air flow has already passed through the substrate and extracted vapor. However, this does little to increase the actual efficiency of the extraction as it has already taken place by the time the full useful Venturi-induced acceleration of the convective hot air flow takes place.

The present art provides for specific material, physical, and dimensional relationships causing the helpful Venturi-induced acceleration to take place both prior to and after the extraction has taken place, resulting in a considerable increase in extraction efficiency. In the both the present invention's preferred form with the use-specific, medical grade heat tool, or in it's secondary form using a thermo-coupled hot air gun as the heat source, the intra-convertible nature, extraction efficiency optimization elements in the various extraction apparatuses provided for, oxidation minimizing, and moisture conditioning capabilities all contribute to a clear and substantial improvement to the art as disclosed by Wheeler.

Storz discloses a system that makes it possible to flow the hot air through the portion of plant material to be vaporized or the fluid with one pass, and yet make it possible that inhalation can occur independently and comfortably in multiple inhalations. In order to accomplish this, Storz has provided for a temperature regulated forced hot air base unit, on which the user sits a mated extraction chamber and valve that is connected to a collection balloon. The hot air then flows through the extraction chamber, extracts the vapors. The vapors are then collected in the balloon, which when full can be disconnected below the valve from the extraction chamber and re-connected to a valve housing mouthpiece for delivery purposes.

Although, Storz does disclose a system that meets his stated goal of increasing the convenience of extracting and inhaling aromatic and/or active substance containing vapors, he fails to optimize either the extraction process itself or the delivery means for greatest therapeutic gain by the user. The extraction chamber Storz discloses and demonstrates is a straight bore extraction chamber preferably manufactured from light metal that does not take advantage of the specific material, physical, and dimensional relationships disclosed and demonstrated in the present invention. Such physical and dimensional relationships include tapered intake and vapor delivery vessel volumes that cause the helpful Venturi-induced acceleration of the convective hot air flow to take place both prior to and after the extraction has taken place for a considerable increase in extraction efficiency. Storz's straight bore extraction chamber suffers slow and inefficient extractions as a result and does not accomplish his own stated goal of making it possible to flow the hot air through the portion of plant material to be vaporized or the fluid with one pass. Due to the use of light metal, or in the case of the actual commercially available embodiment of Storz's invention, stainless steel, for the extraction chamber and valve assembly, the extraction chamber suffers from progressively increasing apparent extraction temperatures with the same temperature convective hot air flow passing through because of the undesirable thermo-dynamic qualities of the metal. The steel collects the heat until reaching a point well above the desired vaporization temperature, at which point it radiates heat into the chamber, adversely affecting the quality and purity of the extracted vapor.

The present invention utilizes tapered and o-ring friction-based mating methods for the various apparatus components suitable for use with borosilicate, quartz, ceramic, or other preferred and more medical-oriented materials with thermodynamic qualities superior to metals that help maintain a more stable temperature in the extraction chamber during usage.

Storz also fails to provide for an embodiment that enables moisture conditioning of the vapors prior to delivery and fails to consider the effect the residual collection of sticky vapor condensate on the spring-actuated valve components will have over medium to long term usage periods. In the present invention's preferred embodiment, with the use-specific, medical grade heat tool, or in it's secondary embodiment, using a thermo-coupled hot air gun as the heat source, the intra-convertible nature, extraction efficiency optimization elements, the manually actuated residue resistant valve design, and the moisture conditioning capabilities of the vapor extraction chamber to valve-controlled vapor collection balloon to moisture conditioning vapor delivery vessel configuration all contribute to a clear and substantial improvement over the art as disclosed by Storz.

The current use of cigarettes or smoking pipes for the inhaling of aromatic and active constituents of plants, botanicals and orthomolecular compounds is recognized as delivering numerous irritants and possible carcinogens along with the desired active principles to the tracheobronchial tree and oral cavity. Vaporization, the temperature range of which is represented by the boiling points of the desired active constituents, occurs significantly below the flash point and pyrrolytic temperature of both the active and non-active components of commonly smoked materials, and thus, as a delivery medium, separates out the more therapeutic and active chemical components from the crude plant or resin impurities and breakdown products of pyrrolsis. The various vaporization systems that have been developed over the years to harness the advantages of this delivery medium have all suffered from one or more weaknesses.

The currently used means by which to vaporize aromatic and active plant and orthomolecular materials for Hot Gas Extraction Aromatherapy and Medical or Phyto-Inhalation include several different approaches.

The Atomization approach, where the aromatic and active compounds are extracted from the substrate using a solvent such as alcohol, and then the mixture is atomized into a vapor or mist that can be inhaled.

The Combined Thermal/Solvent approach, where the aromatic and active compounds are extracted from the substrate using a solvent, and then the mixture is heated until a vapor is formed that is allowed to diffuse into the ambient atmosphere.

The Combustion Smoking approach, or smoldering of various plant and botanical materials or concentrates (previously extracted oils and resins), where the smoke produced through combustion of the substrate contains a small amount of the aromatic and active compounds in vapor form, which is inhaled simultaneously with the smoke.

The Thermal Conductive approach, where a hot surface is used to heat the substrate until the vapors release and then are either inhaled directly or captured for subsequent delivery.

The Thermal Convective approach, where four different distinct sub-approaches exist: heat guns with thermo-coupled controllers that are not accurate enough for a medical level of accuracy and fan motors that are not brushless (so could potentially release carbon ions) are used with special extraction chamber bowls attached to conventional pipes or vapor specific inhalation vessels; soldering iron elements with glass or metal extraction chamber housings hooked up to a mouthpiece or hose that are passive convective and rely on the inhalation of the user and are not thermo coupled controlled so that the amount of inhalation force a user uses will dramatically affect the temperature at the actual extraction point; or aluminum elements such as are used in the terrarium business for keeping reptile tanks warm (which are also not accurate enough for medical level therapeutic applications) are used within a housing as a heat source for vapor specific extraction and delivery systems that either use a hose for direct dry delivery and inhalation or use a balloon attached to a valve controlled extraction chamber for filling, and then a valve containing mouthpiece for dry delivery of the balloon captured vapor.

This last system has solved the problem of previous vapor capture and delivery approaches that did not let the user easily move with the captured vapor and suffered from uncontrolled oxidation of the vapor by using a balloon that could be collapsed and rid of all air in order to minimize oxidation. It is light and easy to hold. However, it's straight bore extraction chamber makes for a slow, inefficient extraction and its delivery mouthpiece enables only a dry delivery.

The Thermal Convective and Conductive Combination Approach is a generally unintentionally attained category where all of the previous Thermal and Convective systems end up to varying degrees during prolonged usage depending largely upon the materials chosen for manufacturer, and thus, include both indirect and direct inhalation systems. The Thermal Convective and Conductive Combination Approach is preferred in cases where oil, fluid, or fine powder concentrates are used as the extraction substrate because they do not readily expose much surface area for efficient convective extraction alone.

SUMMARY

Besides offering functional technological advantages over the prior art, the present invention also offers an economic and application advantage over the prior art by offering the intra-convertibility of a single heat source compatible with multiple apparatuses to allow for the selection of the extraction chamber and delivery method best suited for the user circumstance and substrate used and/or vapor concentration desired without the expense of multiple heat sources.

The present invention incorporates an intra-convertible thermo-coupled convective heat source and multiple compatible processes and apparatuses for extraction and delivery of aromatic and active substance containing vapors of plant materials and/or fluids and/or extracts and/or orthomolecular compounds via hot air. It provides a more economical, flexible, and broadly applicable approach to vaporization for therapeutic applications in comparison to single process and apparatus systems currently available as the health care practitioner will be enabled to better match the system to the circumstances of the patient and the particular desired vapor therapy, rather than the other way around, without the expense of multiple, non-cross compatible systems.

The present invention allows a single, effective heat source to be used in twelve different process and apparatus configurations and also improves the quality of the extractions and delivered vapor thereof through improvements achieved via well-known material, physical, and dimensional relationships. These well-known material, physical, and dimensional relationships such as those that induce the Venturi effect, as explained by Bernoulli's principle, offer clear and mathematically demonstrable advantages over existing designs in the field.

The present invention also makes it possible to improve the safety and ergonomics of the various processes and apparatuses included in its cross-compatible platform.

Because the physical characteristics of the present invention in six of the twelve configurations allow it to be easily adapted to be compatible with common smoking pipe designs currently in use by using the intra-convertible heat source's temperature specific, constant hot air flow to cause the release of the active components in vapor form from substrate held within the traditional smoking pipe bowl or one of two different specialized extraction chambers adapted for use with either dry or moisture conditioned pipe designs in lieu of flame from matches or a lighter as a source of ignition whereas the active components would be delivered concurrently with numerous irritants and possible carcinogens in the smoke that is a result of combustion, it is thus conducive to popular use as it will involve similar processes and rituals as popularly used for smoking and, as such, represents a harm-reduction technology that could benefit many current pipe smokers.

Because the physical characteristics of the present invention in one the twelve configurations enables vapor extraction from traditional cigarettes or cigars, it represents a harm-reduction technology that could benefit many current cigarette or cigar smokers.

Because the physical characteristics of the present invention in nine of the twelve configurations (apparatuses used in four configurations are structurally similar to systems commonly used for both combustion smoking and vaporization) enable improved vapor extraction and delivery from plant materials and/or fluids and/or extracts and/or orthomolecular compounds over other structurally comparable, single function systems, it represents an improvement in available technology that could benefit many current hot gas extraction aromatherapy or phyto-inhalation health care practitioners and users.

The present invention expands the usefulness of common smoking pipe apparatuses to offer a more health conscious, safer, and more efficient delivery medium than incineration or combustion for the aromatic oils in tobacco and other commonly smoked herbs. The delivery system is vaporization.

The present invention offers three ways to accomplish this with the same intra-convertible heat tool. The first way is the simple and crude use of the intra-convertible heat tool, wherein the user simply aims the hot air output at a bowl on one of many common smoking pipe designs. The second way is through modification of the first approach, using a tapered nozzle attachment that enables a substantially airtight mating with the bowl on one of many conventional pipe designs to increase the efficiency of the extraction. The third way is to adapt many common smoking pipe designs with a two piece extraction chamber with a special Venturi-inducing intake design that mates to the intra-convertible heat tool in order to further increase the efficiency of the extraction.

It is therefore an object of the present invention to provide an intra-convertible thermal vapor extraction and delivery system of completely novel design and/or representing clear and substantial improvements upon prior art and/or intended to work in conjunction with, and broaden the range of use for many forms of commonly used smoking pipes, smoking apparatuses, and other hot gas extraction vaporization-specific methods and apparatuses.

It is another object of the present invention to provide an intra-convertible thermal vapor extraction and delivery system with many advantages and benefits over traditional smoking and other means of vaporization, while maintaining the cost effectiveness, convenience, and desirability of operation to enable accessibility by the general public, and allowing the system to be easily manufactured and marketed.

It is a further object of the present invention to be of a basic design to enable durable and reliable construction out of a variety of materials, especially those preferred for FDA compliance and medical grade manufacturing.

An even further object of the present invention is to provide an intra-convertible thermal vapor extraction and delivery system which is susceptible of low cost of manufacture with regard to both materials and labor, and which accordingly is then susceptible of low prices of sale to the consuming public, thereby making such a an intra-convertible thermal vapor extraction and delivery system economically available to the buying public.

Still yet another object of the present invention is to provide an intra-convertible thermal vapor extraction and delivery system which provides in the apparatuses and methods of commonly used smoking pipes, smoking apparatuses, and hot gas extraction vaporization-specific systems, a system to be used in conjunction with or improve upon the purposes and advantages thereof, while simultaneously offering the selective broadening of the range of uses therewith.

DESCRIPTION OF THE DRAWINGS

FIG. 1A is an orthographic cross-sectional view of the intra-convertible heat tool in hand operative mode and offering an exposed perspective of the internal features;

FIG. 1B is an assembled orthographic view of the intra-convertible heat tool in hand operative mode;

FIG. 1C is an orthographic cross-sectional view of the intra-convertible heat tool in cradle operative mode and offering an exposed perspective of the internal features;

FIG. 1D is an assembled orthographic view of the intra-convertible heat tool in cradle operative mode;

FIG. 2A is a partially separated orthographic cross-sectional view of the intra-convertible heat tool in hand operative, conventional smoking pipe bowl compatible mode including the tapered nozzle attachment;

FIG. 3A is a partially separated orthographic cross-sectional view of the intra-convertible heat tool in hand operative, one-piece vapor extraction chamber and dry vapor delivery vessel compatible mode;

FIG. 9A is a partially separated orthographic cross-sectional view of the intra-convertible heat tool in cradle operative, vapor extraction chamber to valve controlled vapor collection balloon compatible configuration;

DETAILED DESCRIPTION

Figure 2B:
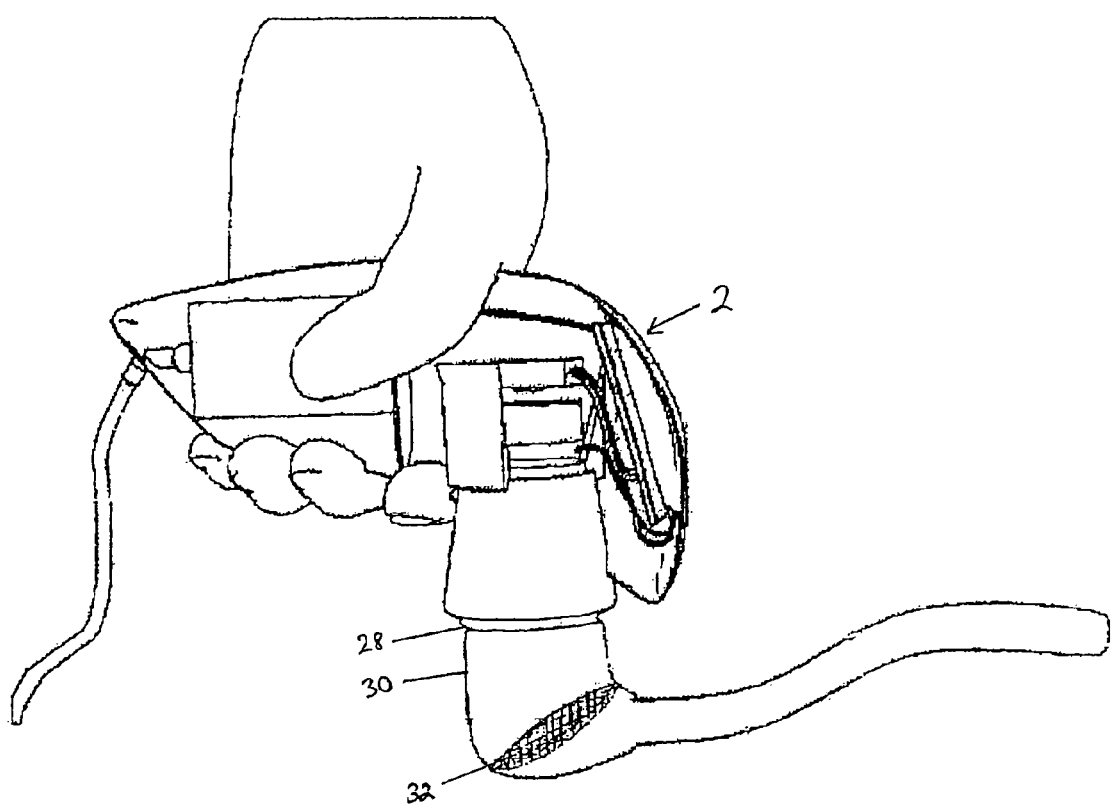
FIG. 2B is an assembled orthographic cross-sectional view of the intra-convertible heat tool in hand operative, conventional smoking pipe bowl compatible mode including the tapered nozzle attachment.

Persons of ordinary skill in the art will realize that the following disclosure is illustrative only and not in any way limiting. Other embodiments of the invention will readily suggest themselves to such skilled persons having the benefit of this disclosure.

The present invention provides an intra-convertible, thermo couple controlled, continuously variable, convective heat source that can be used in a stationary, cradled manner or in a hand held manner in conjunction with conventional smoking pipe designs, cigarettes, and multiple compatible vapor extraction apparatuses of individual merit and application specific usefulness.

These vapor extraction systems and methods include: (1) the crude but moderately effective hand held use of the intra-convertible heat tool by simply aiming it at the bowl on a standard pipe used for smoking; (2) a specialized nozzle attachment to improve mating with conventional smoking pipe bowls when using the intra-convertible heat tool in hand held mode; (3) a specialized one-piece extraction chamber with sequential Venturi-inducing tapered intake and lower chamber that can be retrofitted to conventional dry smoking pipe designs or used with a vapor specific dry delivery vessel for use with the intra-convertible heat tool in hand held mode; (4) a specialized one-piece extraction chamber with sequential Venturi-inducing tapered intake and lower chamber that can be retrofitted to conventional moisture conditioning smoking pipe designs or used with a vapor specific moisture conditioning delivery vessel for use with the intra-convertible heat tool in hand held mode; (5) a specialized two-piece extraction chamber with sequential Venturi-inducing tapered intake and lower chamber that can be retrofitted to conventional dry smoking pipe designs or used with a vapor specific dry delivery vessel for use with the intra-convertible heat tool in hand held mode; (6) a specialized two-piece extraction chamber with sequential Venturi-inducing tapered intake and lower chamber that can be retrofitted to conventional moisture conditioning smoking pipe designs or used with a vapor specific moisture conditioning delivery vessel for use with the intra-convertible heat tool in hand held mode; (7) a two-piece extraction chamber with a sequential Venturi-inducing tapered intake and upper chamber, and a delivery hose to a mouthpiece for use with the intra-convertible heat tool in cradled, stationary mode; (8) a two-piece extraction chamber with a sequential Venturi-inducing tapered intake and upper chamber, and a delivery hose to a delivery vessel that contains water, other liquid, and or ice for moisture conditioning of the vapor for use with the intra-convertible heat tool in cradled, stationary mode; (9) an extraction apparatus comprised of a two piece extraction chamber with substrate suspending screen and sequential Venturi-inducing tapered intake and upper chamber housing a valve operated with a dual purpose substrate tamp and valve prop in communication with a vapor capture balloon that, when filled, is detached from the intake and lower extraction chamber at the valve housing upper chamber, and in turn mated to a mouthpiece shaped delivery tube for dry inhalations and gravity enabled user position controlled valve action or alternatively a delivery tube and valve prop for insertion into a delivery vessel that contains water, other liquid, and or ice for moisture conditioning of the vapor, where the valve prop is positioned to open the valve and the liquid acts as a secondary containment valve; (10) a specialized nozzle attachment with a perforated needle-like shape for the intra-convertible heat tool that mates with common cigarettes or cigars to enable vapor extraction from the rolled up tobacco or other plant substrate; (11) a specialized extraction chamber with sequential Venturi-inducing tapered intake and upper chamber and capture tube with cooling coils housed within a container for holding water and/or ice or other cooling substance for collecting vapor condensates; and (12) an open-air environmental diffuser assembly for extracting and then diffusing mixed water and oil vapors into the ambient surroundings for passive rather than direct inhalation.

Furthermore, the present invention enables the multi-approach smokeless, thermal vaporization of and effective delivery of the active constituents in plants, botanicals, and orthomolecular compounds with many of the advantages and individual elements of conventional smoking mediums and various vapor extraction and delivery apparatuses, systems and methods without the need for multiple heat sources, thus avoiding the additional costs and inconstant temperature standards that result.

Tobacco and medicinal herb smokers will be able to use the intra-convertible heat tool of the present art in conjunction with common pipe designs currently in use by simply setting the temperature appropriately for the substrate being used and aiming the intra-convertible heat tool's output nozzle at conventional pipe bowls containing the substrate to enable the delivery of hot air extracted vapor in lieu of using a flame from a lighter or match as a source of ignition for the purpose of combustion smoking.

Smokers will also be able to further improve the harm reduction capabilities and extraction efficiency of such an approach by modifying the intra-convertible heat source of the present invention with a specialized nozzle attachment, or by modifying their pipes with specialized extraction chambers that take the place of conventional bowls that are compatible with the intra-convertible heat tool in hand held mode and are made specifically for such a hot gas vapor extraction process. If the smokers prefer cigarettes, they will be able to use a specialized nozzle attachment extraction apparatus for use with cigarettes.

The specialized nozzle attachment, extraction chambers, other vapor extraction apparatuses, and the cigarette compatible extraction apparatus will be described in more detail. They all are cross compatible with the same intra-convertible heat tool of the present invention. This would be helpful for people with immune deficiencies and healthy people alike using herbs medically or smoking tobacco or herbs. It would enable the delivery of the actives to the tracheobronchial tree via the oral cavity without the numerous irritants and possible carcinogens contained within the smoke, while still maintaining the convenience and familiarity of conventional smoking techniques and apparatuses, with the added flexibility and economic advantage of choosing one of twelve different extraction and delivery methods without needing a different heat tool for each method.

Since Hot Gas Extraction Aromatherapy and Medical or Phyto-Inhalation practitioners will be able to use multiple extraction apparatuses with the same heat tool, the present invention will offer a savings of money and increase in the effectiveness of their professional treatments by offering more diversity in application, without the need for purchasing multiple complete systems, and more consistent results, as the heat source will be common for all systems. The practitioner will be able to match the system to the patient instead of the other way around. The practitioner will also be confident with the temperature settings or range given for use. Each of the extraction apparatuses and methods disclosed in the present invention offer unique and specialized features inherent to their prospective designs. Currently, the full range of effective extraction apparatuses are only available as part of individual systems that must be purchased separately, tuned separately and have optimal extraction temperatures determined separately. None of them contain any cross-compatible or intra-convertible elements. This creates difficulty in establishing usage and quality standards important to any sort of medicinal practice and is cost prohibitive for practitioners that would like to be able to use multiple systems and methods.

Since the present invention can be effectively used to enable the rapid-onset delivery of the active compounds in an extremely broad range of herbs and botanicals conventionally utilized therapeutically in the form of teas, tinctures, oils, capsules or pills, it offers many advantageous over these traditional delivery mediums because the rapid-onset delivery enabled by vapor inhalation as opposed to the much slower metabolic delivery process allows for easier self-titration by the user and faster acting therapeutic effects.

In FIGS. 1 through 13C, schematic type drawings are utilized to represent the embodiments of various usage modes and extraction and delivery configurations of the present invention, wherein like elements are numbered alike. The intra-convertible heat tool 2 in one of its two operational modes may be compatible with twelve possible vapor extraction and delivery methods and apparatuses.

FIGS. 1A and 1B illustrate the intra-convertible heat tool 2 in hand operative mode, representing the present invention in its preferred form. FIG. 1A offers an exposed perspective of the internal features of the preferred embodiment.

FIGS. 1C and 1D illustrate the intra-convertible heat tool 2 in cradle operative mode, representing the present invention in its preferred form, in stand alone operational prepared mode, with no compatible extraction apparatus depicted.

Heat tool 2 comprises medical grade elements. Heat tool 2 comprises casing 4, which is configured to fit easily and comfortably within in the grasp of the user's hand. Casing 4 may be an ergonomically shaped, high temperature resistant plastic casing resistant to high temperature. Heat tool 2 also comprises an output nozzle 6, preferably made of stainless steel, ceramic-coated metal or ceramic. Internal nozzle insulation sleeve 22 surrounds output nozzle 6. Output nozzle 6 may comprise vortical flow inducing bodies/spokes 7 for improving the delivery of the hot air output. Nozzle sleeve 22 is preferably made of ceramic. Heating elements are well known in the art. Heating element 10 on heat tool 2 is preferably a ceramic dipped or quartz encapsulated heating element. However, it is contemplated that a variety of heating elements may be used, such as an aluminum honeycomb wafer. Fan 18 is positioned behind heating element 10 for blowing ambient air through the element for heating it to the desired temperature and forcing it out output nozzle 6. Fan 18 is preferably brushless.

Heat tool 2 may also comprise power control board 12 for temperature and fan control. Power control board 12 is preferably silicon dipped. Additionally, heat tool 2 may include LCD temperature display and control monitor 14 and power, temperature, and fan controls 16 provided on the outside of casing 4. Heat tool 2 may comprise a power converter/battery compartment 26 for housing a battery or power converter. The power components, such as power control board 12, may be silicon sealed or surrounded by solder-less contacts in accordance with medical and safety standards.

Heat tool 2 may be unsubstantially mated to a bowl on a standard smoking pipe design in hand held user directed mode. "Unsubstantially mated" refers to a operational coupling that lacks a substantially sealed pathway, whereas "substantially mated" refers to coupling that has a substantially sealed pathway.

Heat tool 2 may also be used in cradle mode. Cradle 8 is configured to accept casing 4 in a manner that points output nozzle 6 vertically up. Cradle 8 preferably has a substantially planar bottom surface in order to allow for cradle 8 to rest on a flat surface in a stable position. Additionally, cradle 8 preferably has an upper surface that is concave for holding casing 4. Cradle 8 and casing 4 are preferably sized and shaped in a complimentary manner so as to allow cradle 8 to securely hold casing 4.

Although not shown, casing 4 may have a portion of its bottom surface (the surface opposite output nozzle 6) that is substantially planar, enabling the casing 4 to rest on a substantially planar surface in a stable position without the use of cradle 8, and with output nozzle 6 directed straight up.

Figure 2C:
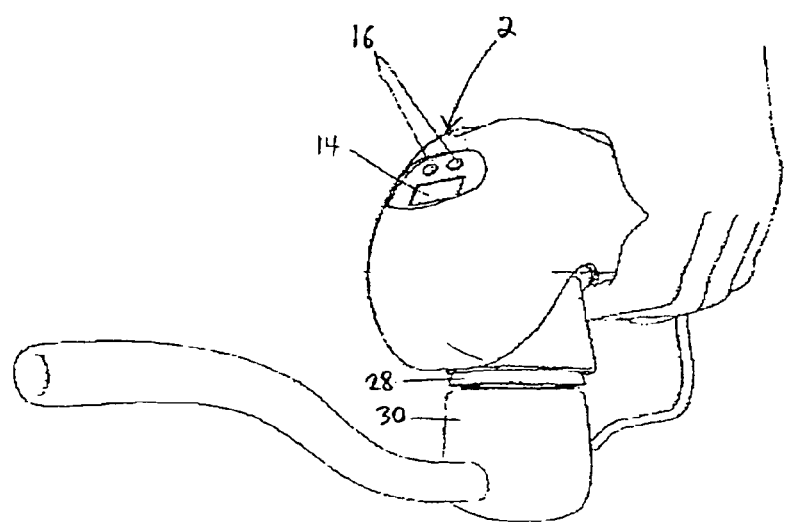
FIG. 2C is an assembled orthographic view of the intra-convertible heat tool in hand operative, conventional smoking pipe bowl compatible mode including the tapered nozzle attachment.

FIGS. 2A through 2C illustrate the intra-convertible heat tool 2 in hand operative, conventional smoking pipe bowl compatible mode, representing one of the twelve configurations of the present invention. Heat tool 2 may be substantially mated to a tapered nozzle attachment 28 and, in turn, to a bowl on a standard smoking pipe 30 having screen 32. The mating to tapered nozzle attachment 28 may improve mating in hand-held user-directed mode.

Figure 3B:
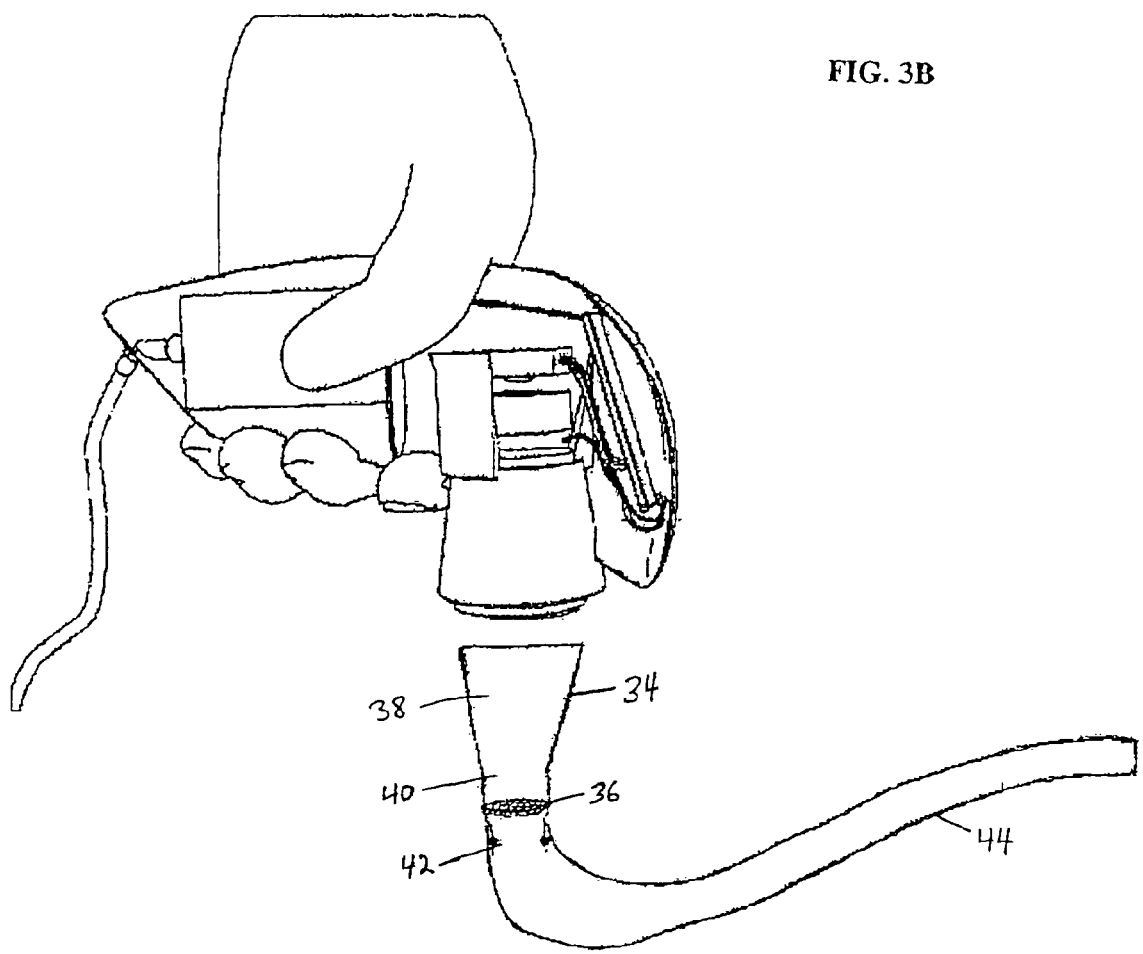
FIG. 3B is an assembled orthographic cross-sectional view of the intra-convertible heat tool in hand operative, one-piece vapor extraction chamber and dry vapor delivery vessel compatible mode.
Figure 3C:
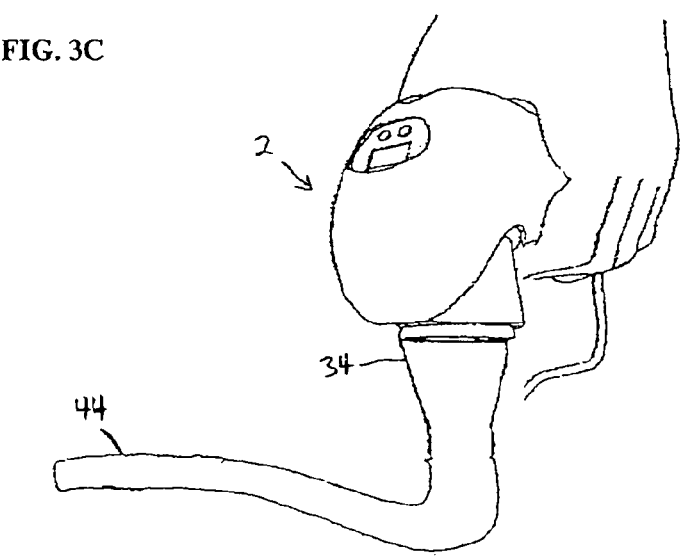
FIG. 3C is an assembled orthographic view of the intra-convertible heat tool in hand operative, one-piece vapor extraction chamber and dry vapor delivery vessel compatible mode.

FIGS. 3A through 3C illustrate the intra-convertible heat tool 2 in hand operative, one-piece vapor extraction chamber and dry vapor delivery vessel compatible mode, representing one of the twelve configurations of the present invention. Heat tool 2 may be substantially mated to a one-piece vapor extraction chamber 34 having substrate suspending screen 36, sequential Venturi-inducing tapered hot air intake 38, and lower substrate chamber 40. Vapor extraction chamber 34 also comprises mating delivery tube 42 and is compatible with traditional/conventional dry smoking pipe delivery structures, such as pipe 44, and vapor specific dry delivery structures in hand-held user-directed mode.

Figure 4A:
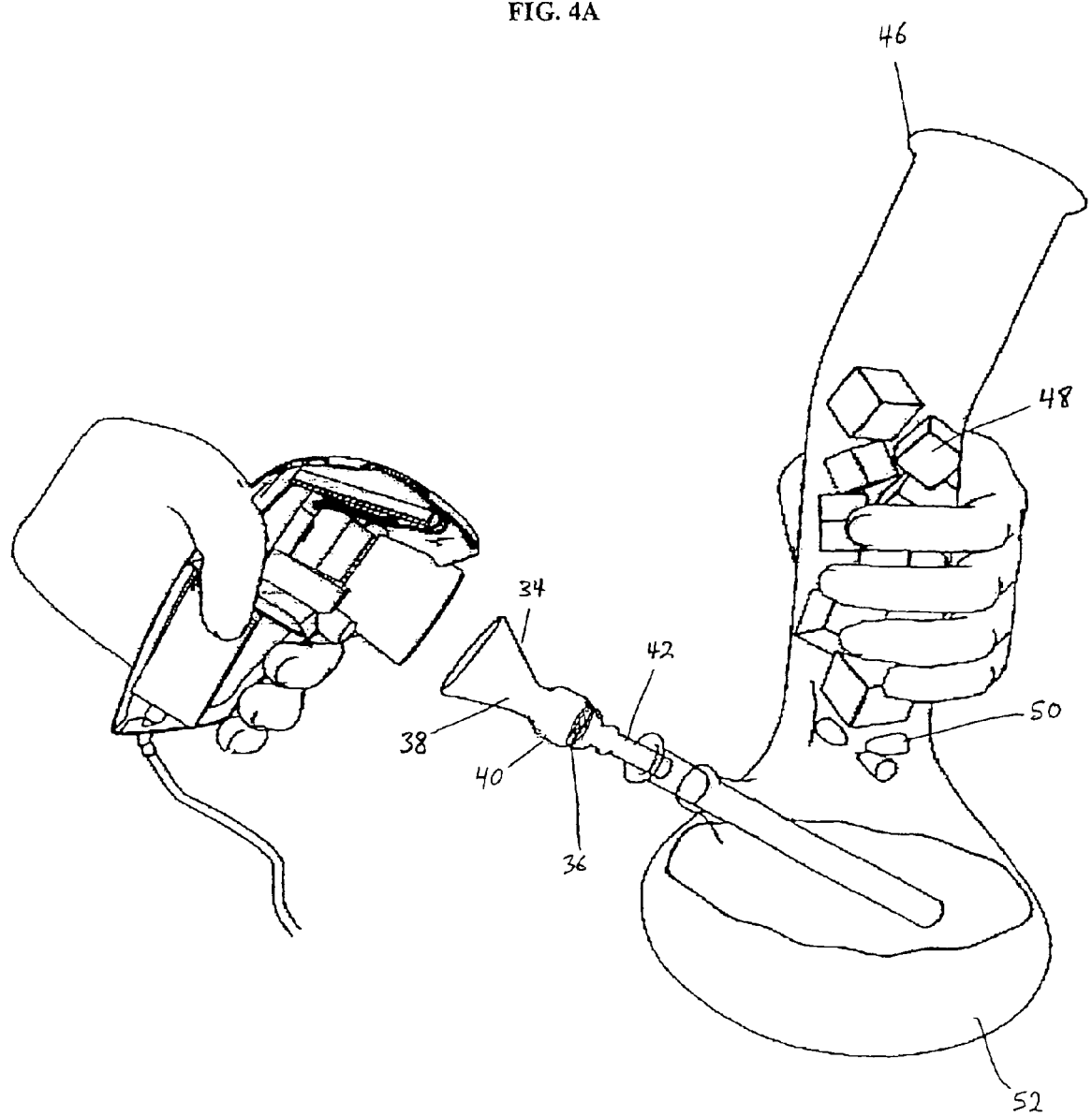
FIG. 4A is a partially separated orthographic cross-sectional view of the intra-convertible heat tool in hand operative, one-piece vapor extraction chamber and moisture conditioning vapor delivery vessel compatible mode.
Figure 4B:
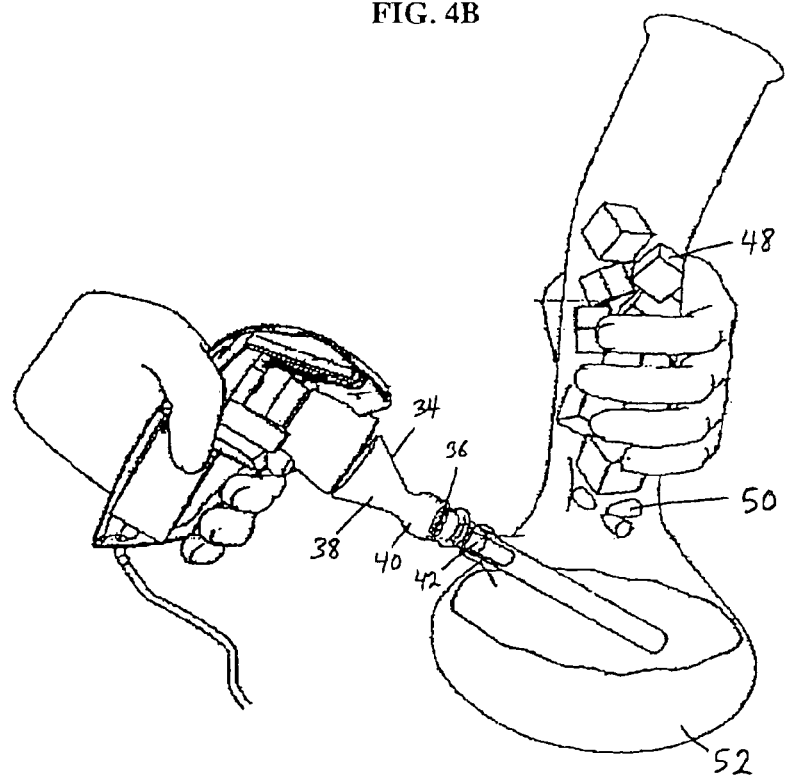
FIG. 4B is an assembled orthographic cross-sectional view of the intra-convertible heat tool in hand operative, one-piece vapor extraction chamber and moisture conditioning vapor delivery vessel compatible mode.
Figure 4C:
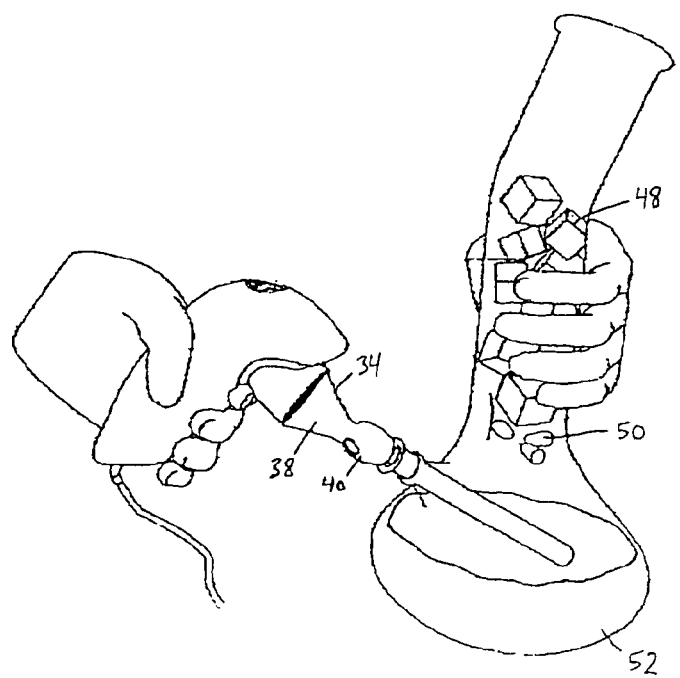
FIG. 4C is an assembled orthographic view of the intra-convertible heat tool in hand operative, one-piece vapor extraction chamber and moisture conditioning vapor delivery vessel compatible mode.

FIGS. 4A through 4C illustrate the intra-convertible heat tool 2 in hand operative, one-piece vapor extraction chamber and moisture conditioning vapor delivery vessel compatible mode, representing one of the twelve configurations of the present invention. Heat tool 2 may be substantially mated to a one-piece extraction chamber 34 with substrate suspending screen 36, sequential Venturi-inducing tapered hot air intake 38, and lower substrate chamber 40. Vapor extraction chamber 34 also comprises mating delivery tube 42 and is compatible with conventional moisture conditioning smoking pipe designs or vapor specific moisture conditioning delivery vessels, such as moisture conditioning vapor delivery vessel 46, in hand-held user-directed mode. Moisture conditioning vapor delivery vessel 46 holds ice 48 and water 52, and may comprise ice catch 50 for preventing ice 48 from falling to the bottom of vessel 46.

Figure 5A:
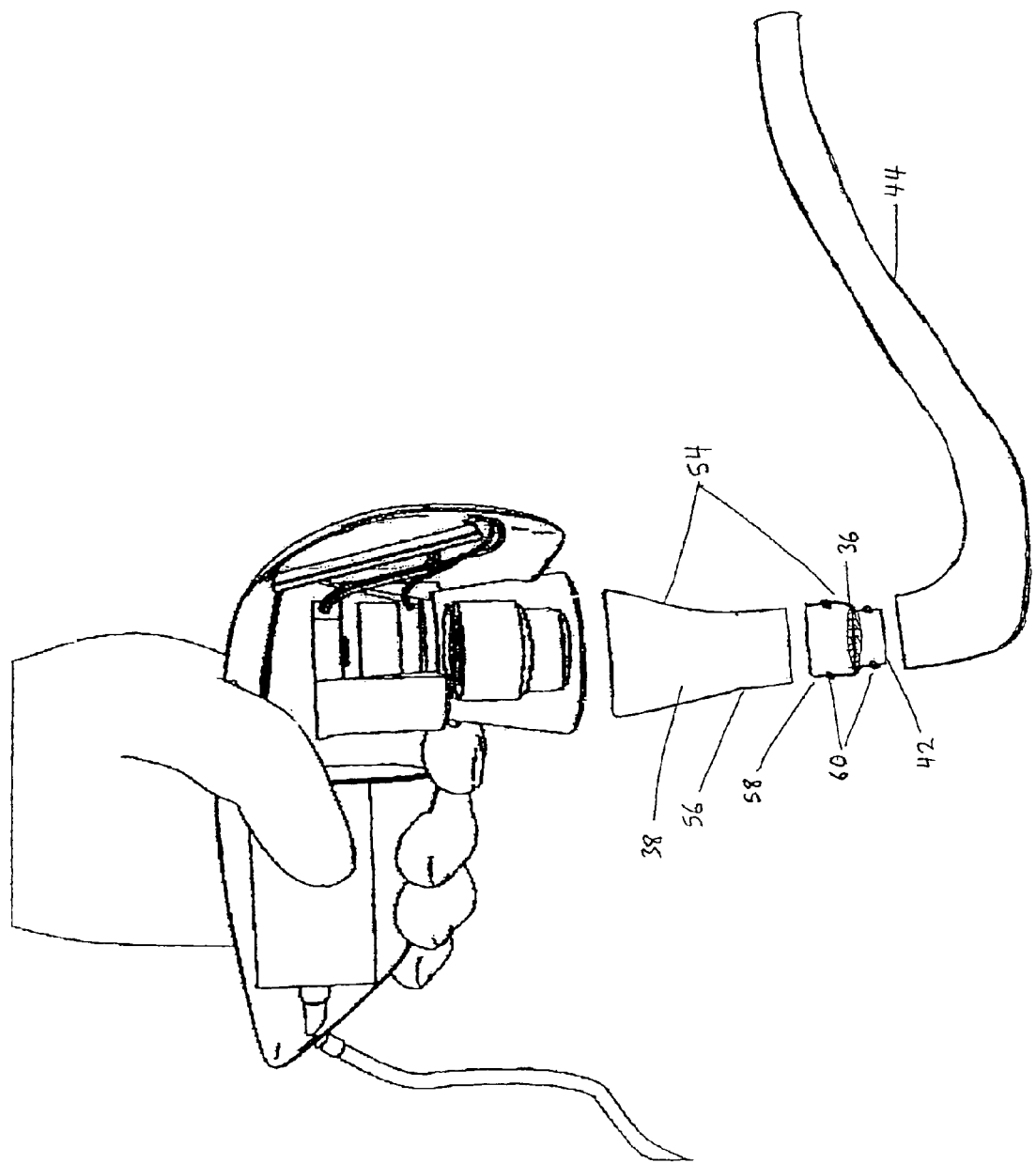
FIG. 5A is a partially separated orthographic cross-sectional view of the intra-convertible heat tool in hand operative, two-piece vapor extraction chamber and dry vapor delivery vessel compatible mode.
Figure 5B:
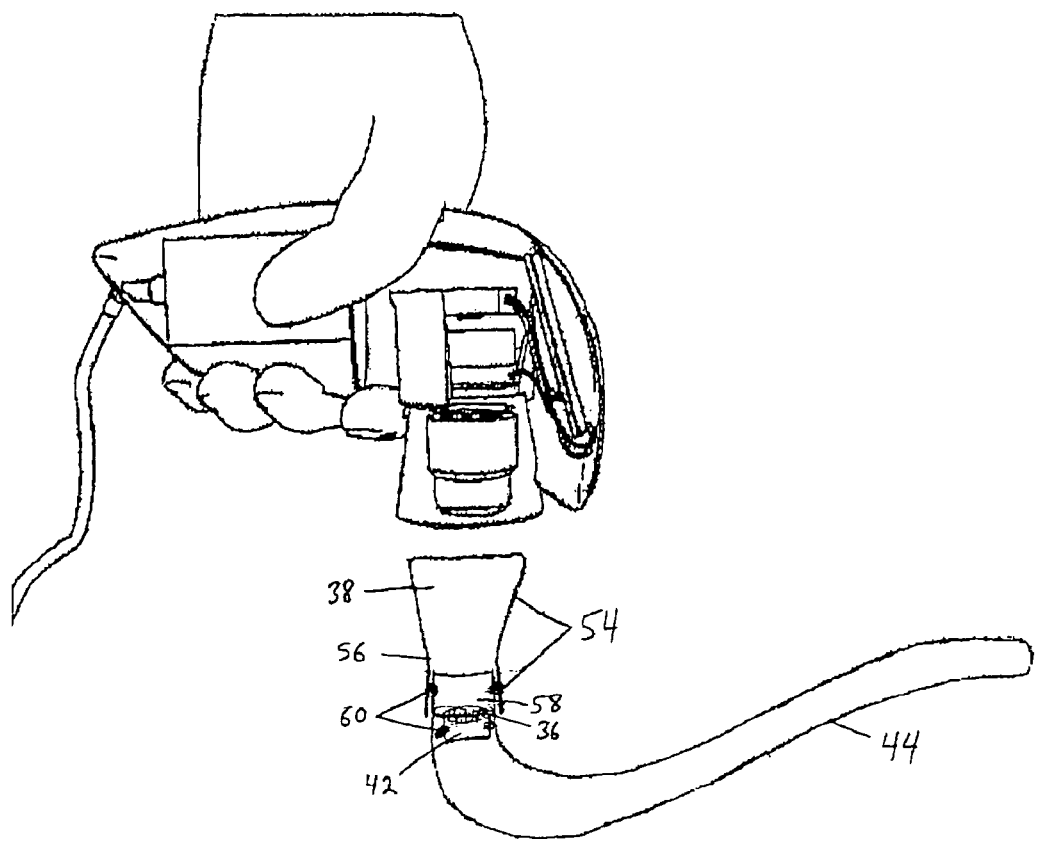
FIG. 5B is an assembled orthographic cross-sectional view of the intra-convertible heat tool in hand operative, two-piece vapor extraction chamber and dry vapor delivery vessel compatible mode.
Figure 5C:
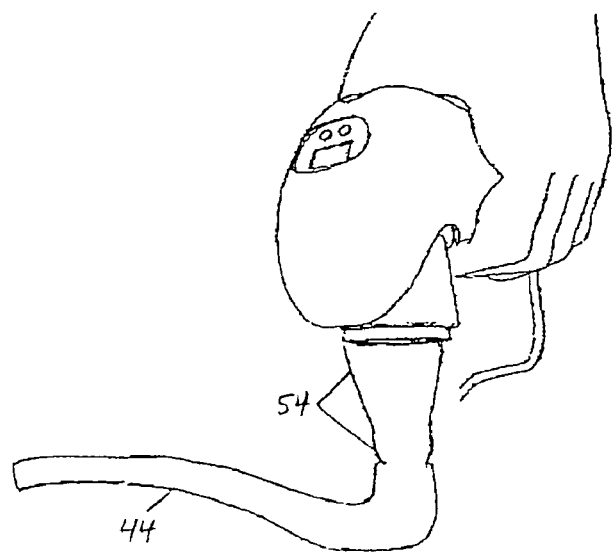
FIG. 5C is an assembled orthographic view of the intra-convertible heat tool in hand operative, two-piece vapor extraction chamber and dry vapor delivery vessel compatible mode.

FIGS. 5A through 5C illustrate the intra-convertible heat tool 2 in hand operative, two-piece vapor extraction chamber and dry vapor delivery vessel compatible mode, representing one of the twelve configurations of the present invention. Heat tool 2 may be substantially mated to a two-piece extraction chamber 54 having upper extraction chamber 56, sequential Venturi-inducing tapered hot air intake 38, lower extraction chamber 58, and substrate suspending screen 36 at the bottom of lower extraction chamber 58. Two-piece extraction chamber 54 also comprises high-temperature O-rings 60 and mating delivery tube 42, and is compatible with conventional dry smoking pipe designs or vapor specific dry delivery structures, such as pipe 44, in hand held user directed mode.

Figure 6A:
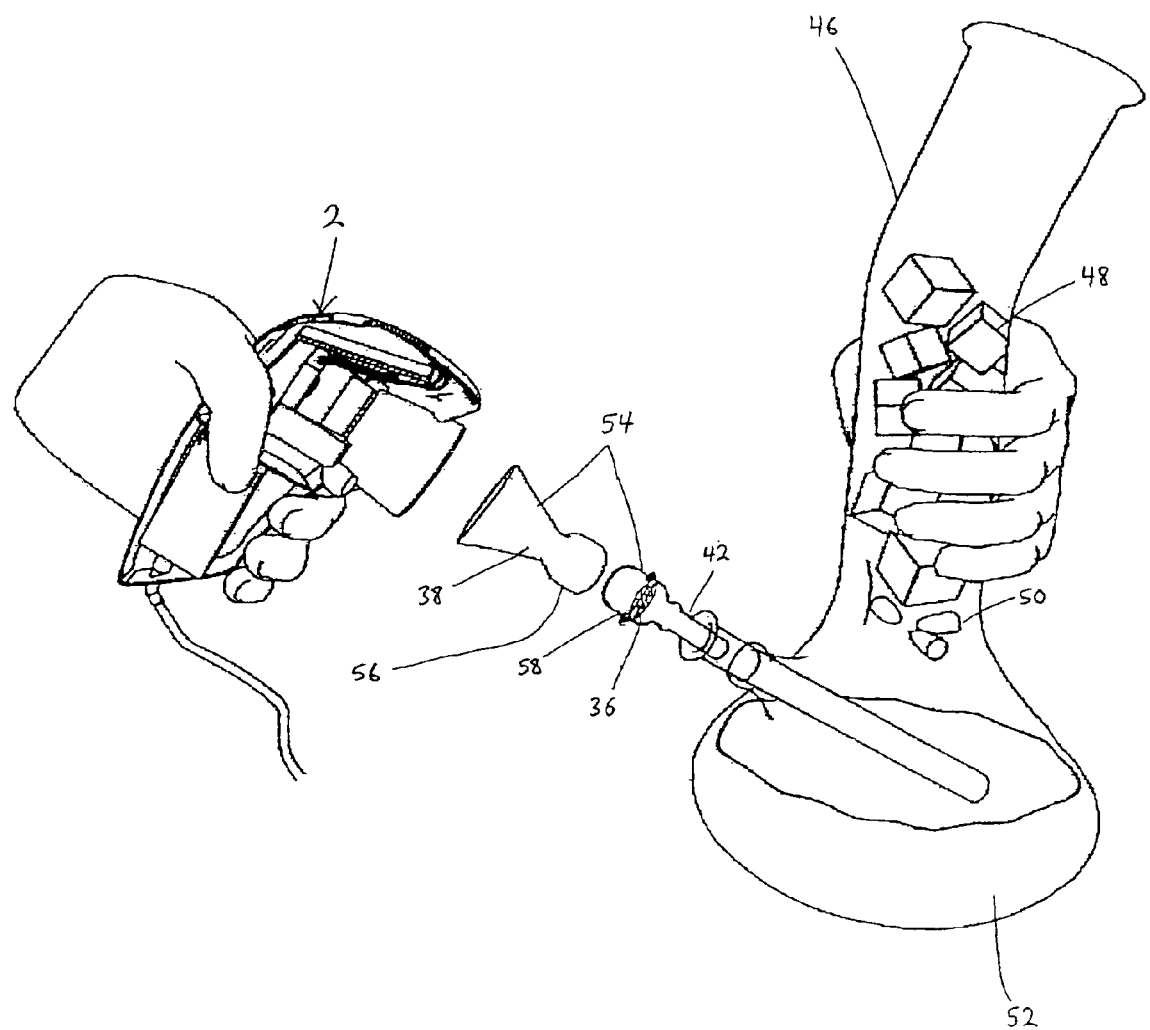
FIG. 6A is a partially separated orthographic cross-sectional view of the intra-convertible heat tool in hand operative, two-piece vapor extraction chamber and moisture conditioning vapor delivery vessel compatible mode.
Figure 6B:
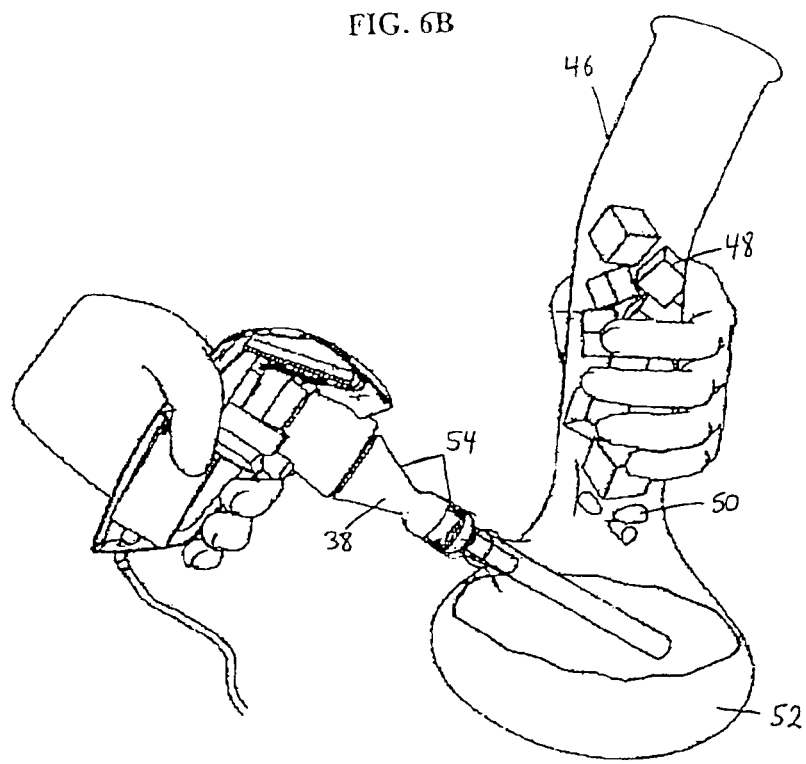
FIG. 6B is an assembled orthographic cross-sectional view of the intra-convertible heat tool in hand operative, two-piece vapor extraction chamber and moisture conditioning vapor delivery vessel compatible mode.
Figure 6C:
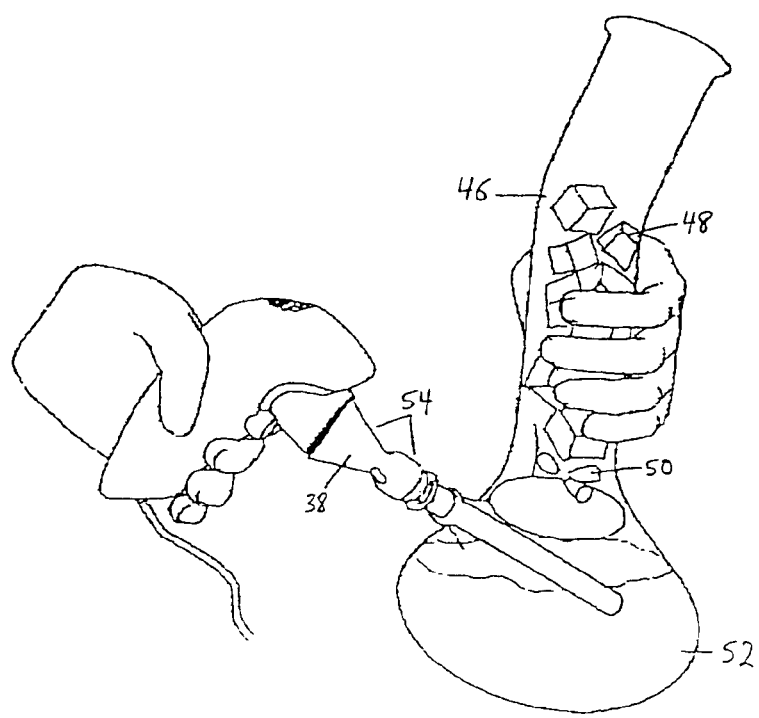
FIG. 6C is an assembled orthographic view of the intra-convertible heat tool in hand operative, two-piece vapor extraction chamber and moisture conditioning vapor delivery vessel compatible mode.

FIGS. 6A through 6C illustrate the intra-convertible heat tool 2 in hand operative, two-piece vapor extraction chamber and moisture conditioning vapor delivery vessel compatible mode, representing one of the twelve configurations of the present invention. Heat tool 2 may be substantially mated to a two-piece extraction chamber 54 having upper extraction chamber 56, sequential Venturi-inducing tapered hot air intake 38, lower extraction chamber 58, and substrate suspending screen 36. Two-piece extraction chamber 54 also comprises mating delivery tube 42 and is compatible with conventional moisture conditioning smoking pipe designs or vapor specific moisture conditioning delivery vessels, such as moisture conditioning vapor delivery vessel 46, in hand held user directed mode.

Figure 7A:
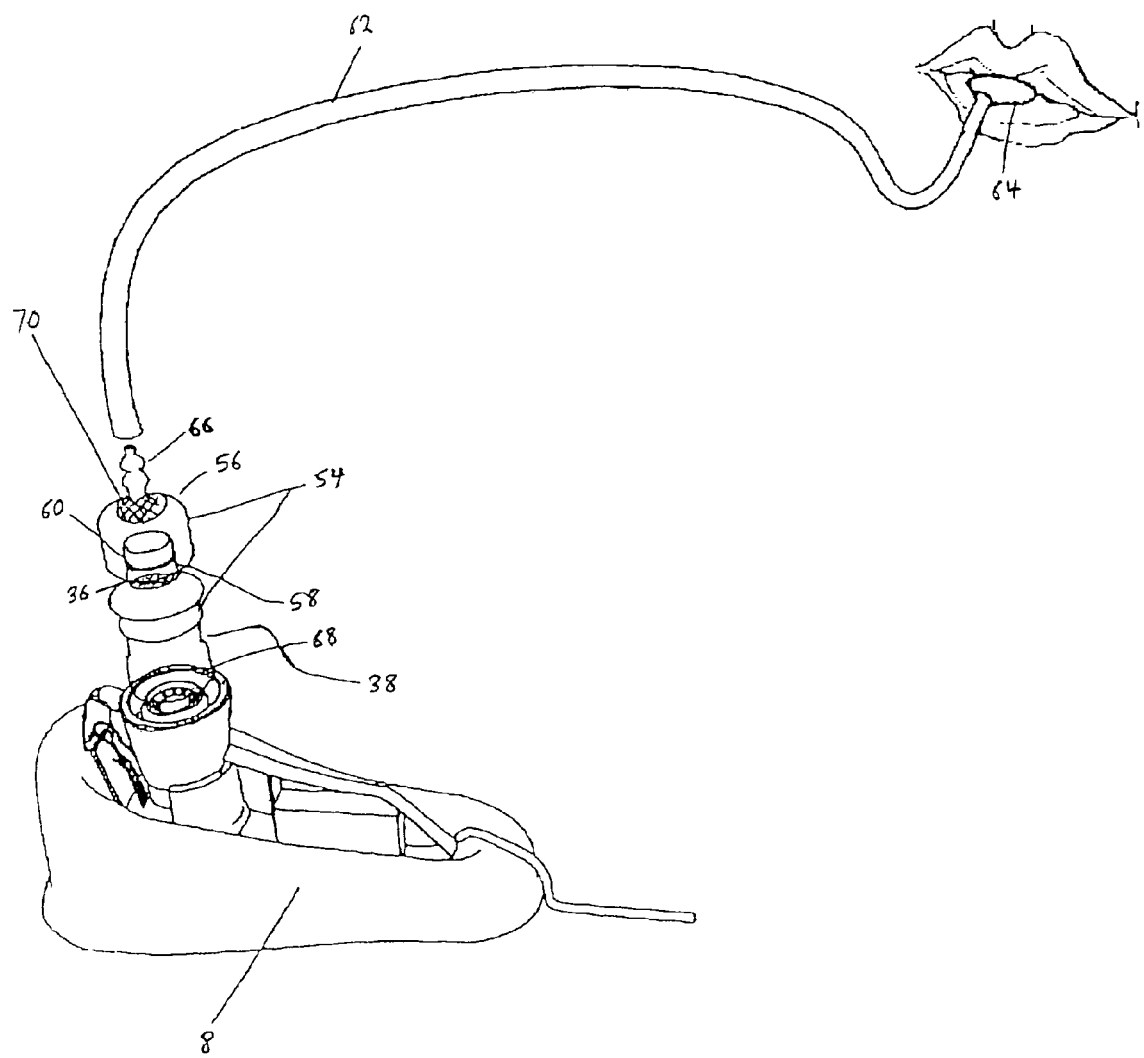
FIG. 7A is a partially separated orthographic cross-sectional view of the intra-convertible heat tool in cradle operative, two-piece vapor extraction chamber to vapor delivery hose compatible mode.
Figure 7B:
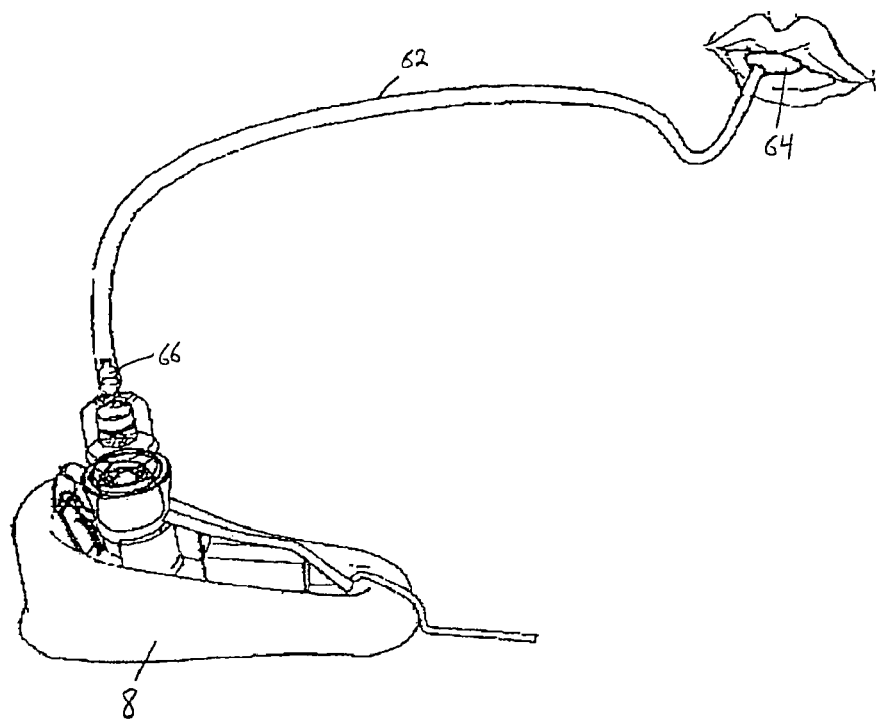
FIG. 7B is an assembled orthographic cross-sectional view of the intra-convertible heat tool in cradle operative, two-piece vapor extraction chamber to vapor delivery hose compatible mode.
Figure 7C:
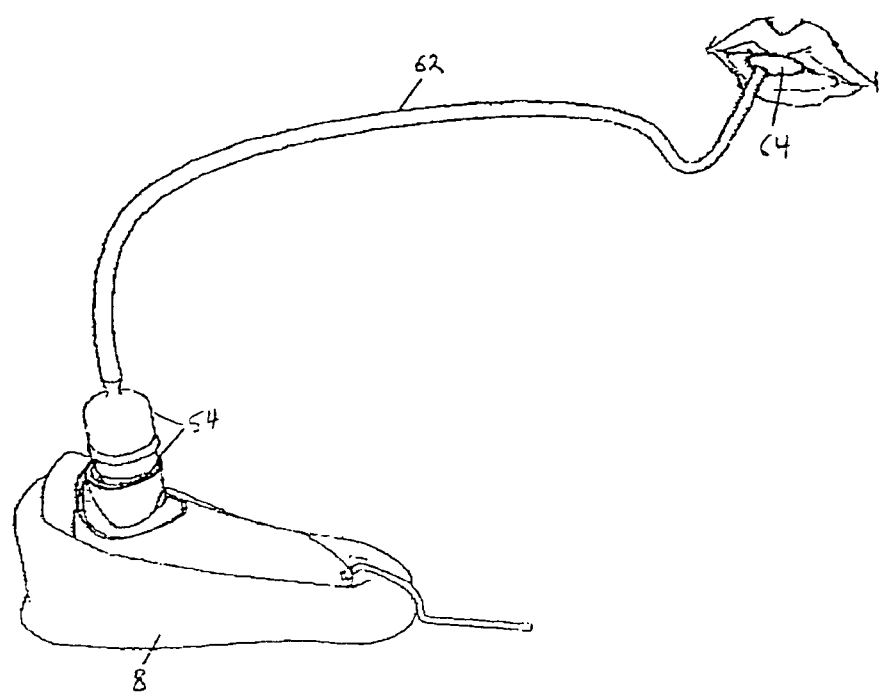
FIG. 7C is an assembled orthographic view of the intra-convertible heat tool in cradle operative, two-piece vapor extraction chamber to vapor delivery hose compatible mode.

FIGS. 7A through 7C illustrate the intra-convertible heat tool 2 in cradle operative, two-piece vapor extraction chamber to vapor delivery hose compatible mode, representing one of the twelve configurations of the present invention. Heat tool 2, held securely in cradle 8, may be substantially mated to a two-piece extraction chamber 54 having substrate suspending screen 36, sequential Venturi-inducing tapered hot air intake 38, upper chamber 56, lower chamber 58, and high-temperature O-ring 60. Two-piece extraction chamber 54 may also have a nozzle seating hip 68, for securing two-piece extraction chamber 54 on output nozzle 6, and substrate containing screen 70. Additionally, two-piece extraction chamber 54 comprises hose nipple 66 and is compatible with a vapor delivery hose 62 having a mouthpiece 64.

Figure 8A:
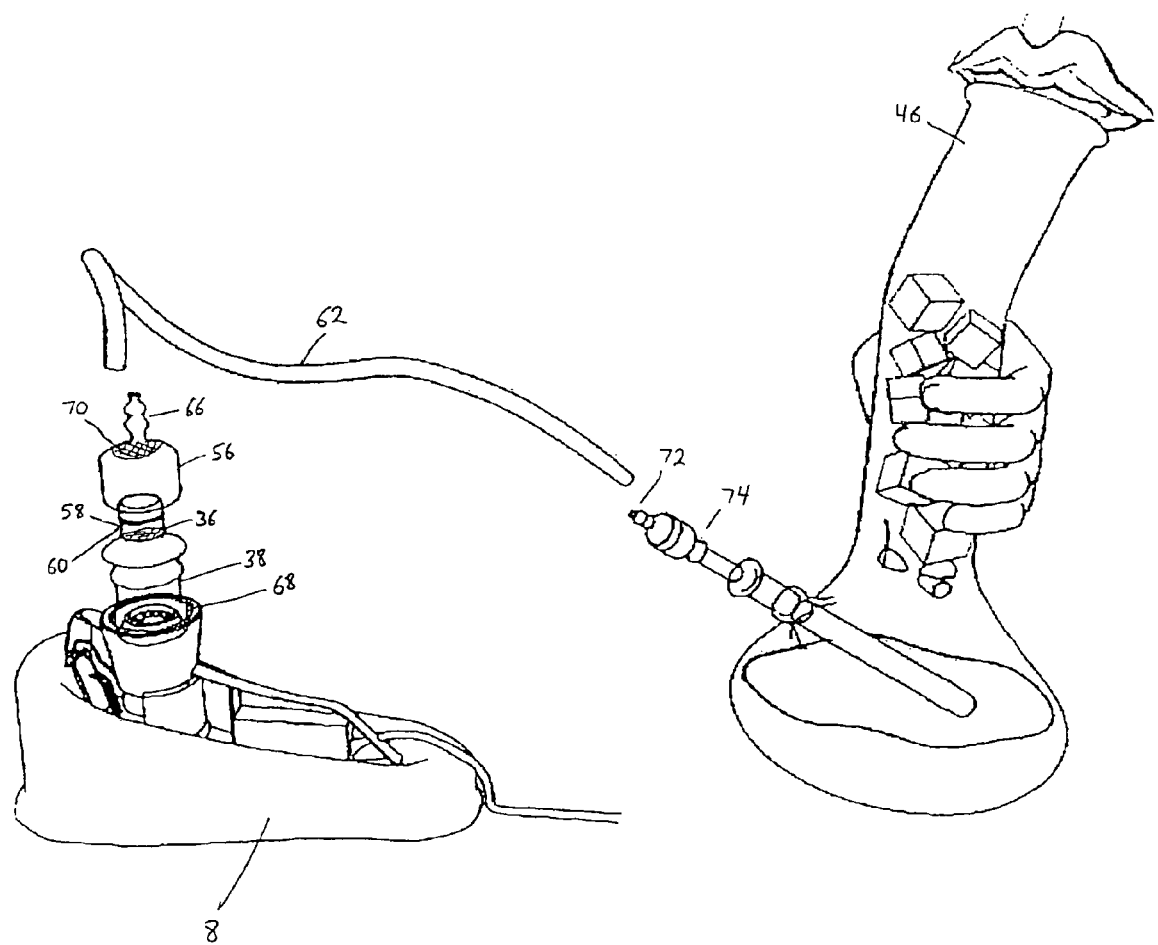
FIG. 8A is a partially separated orthographic cross-sectional view of the intra-convertible heat tool in cradle operative, two-piece vapor extraction chamber to vapor delivery hose to moisture conditioning vapor delivery vessel compatible mode.
Figure 8B:
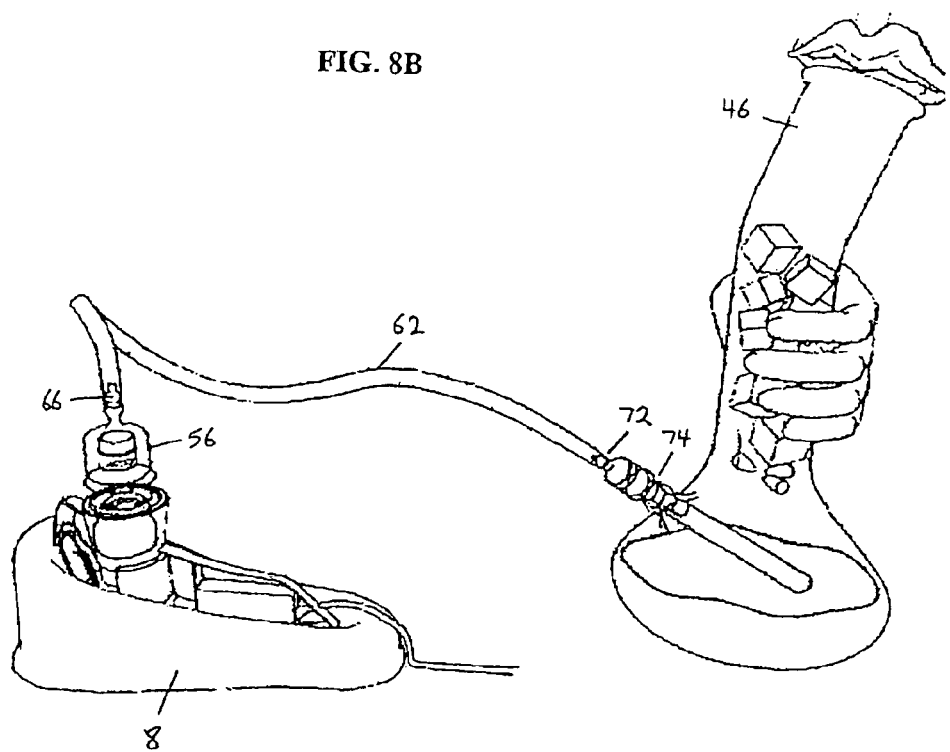
FIG. 8B is an assembled orthographic cross-sectional view of the intra-convertible heat tool in cradle operative, two-piece vapor extraction chamber to vapor delivery hose to moisture conditioning vapor delivery vessel compatible mode.
Figure 8C:
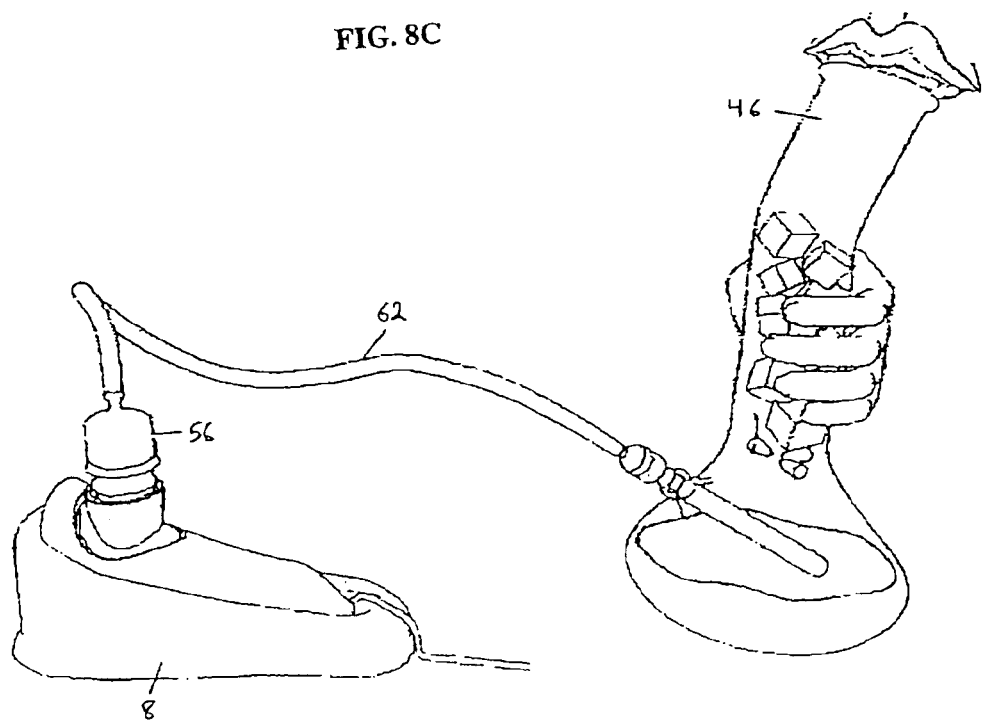
FIG. 8C is an assembled orthographic view of the intra-convertible heat tool in cradle operative, two-piece vapor extraction chamber to vapor delivery hose to moisture conditioning vapor delivery vessel compatible mode.

FIGS. 8A through 8C illustrate the intra-convertible heat tool 2 in cradle operative, two-piece vapor extraction chamber to vapor delivery hose to moisture conditioning vapor delivery vessel compatible mode, representing one of the twelve configurations of the present invention. Heat tool 2, held securely in cradle 8, may be substantially mated to a two-piece extraction chamber having a substrate suspending screen 36, a sequential Venturi-inducing tapered hot air intake 38, upper chamber 56, lower chamber 58, and high-temperature O-ring 60. The two-piece extraction chamber may also have a nozzle seating hip 68, for securing the two-piece extraction chamber on output nozzle 6, and substrate containing screen 70. Additionally, the two-piece extraction chamber comprises hose nipple 66 and is compatible with a vapor delivery hose 62, which is connected to moisture conditioning vapor delivery vessel 46 using delivery hose fitting 72 and mating stem 74.

Figure 9B:
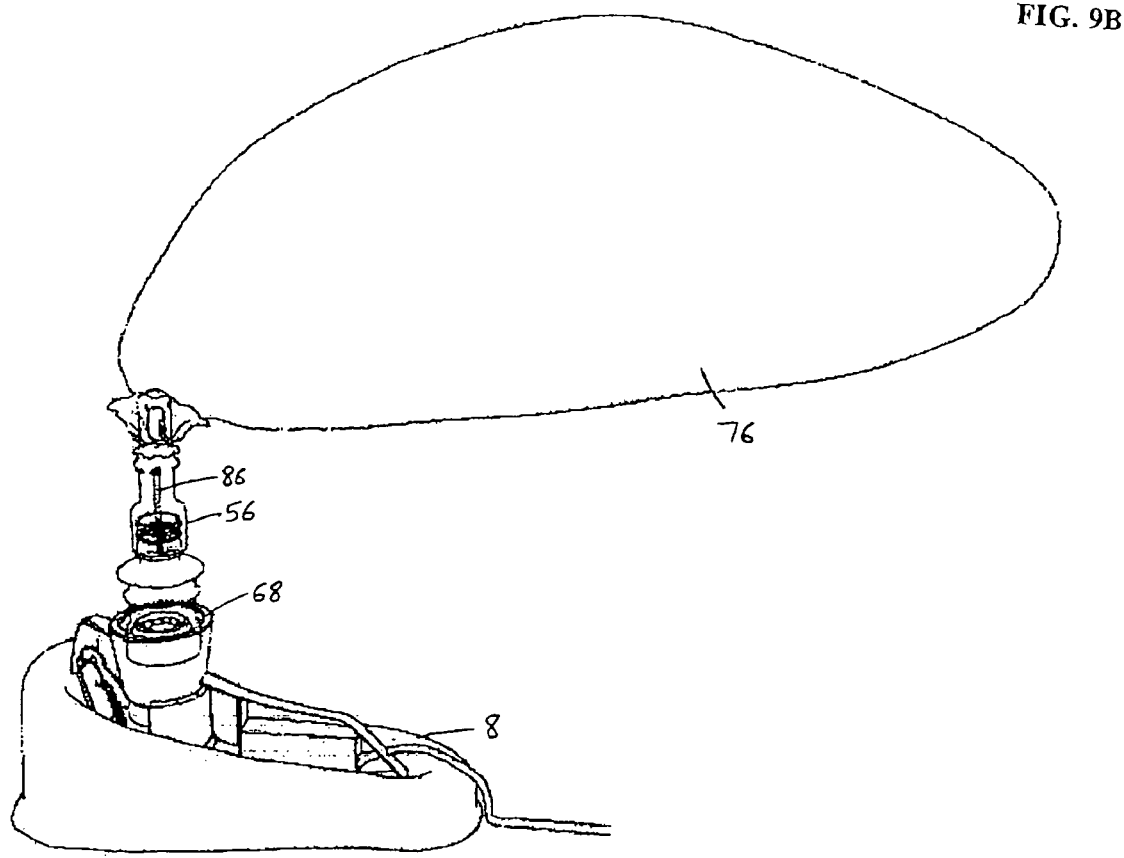
FIG. 9B is an assembled orthographic cross-sectional view of the intra-convertible heat tool in cradle operative, vapor extraction chamber to valve controlled vapor collection balloon compatible configuration.
Figure 9C:
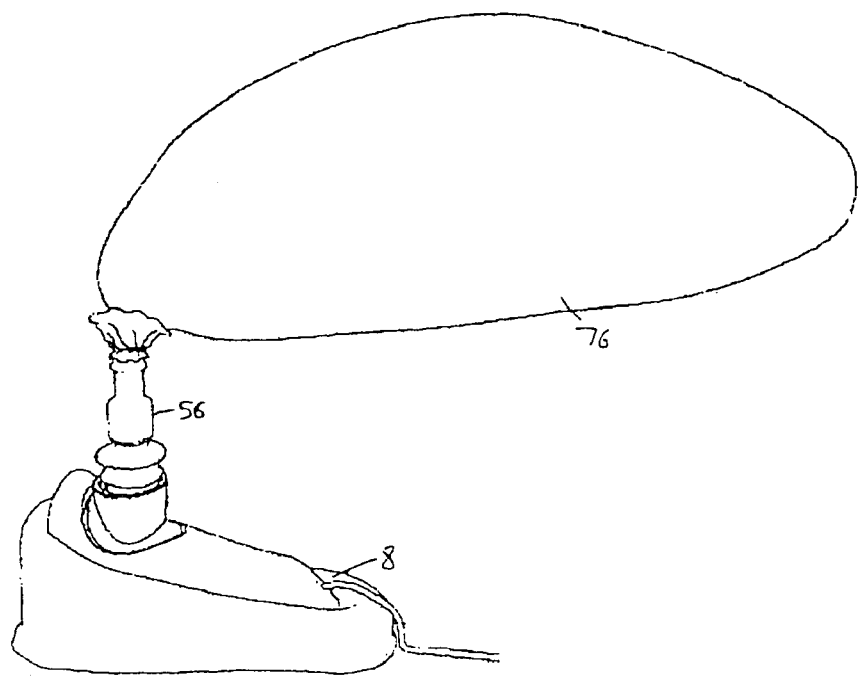
FIG. 9C is an assembled orthographic view of the intra-convertible heat tool in cradle operative, vapor extraction chamber to valve controlled vapor collection balloon compatible configuration.

FIGS. 9A through 9C illustrate the intra-convertible heat tool 2 in cradle operative, vapor extraction chamber to valve controlled vapor collection balloon compatible configuration, representing the first of two basic steps in this method of one of the twelve configurations of the present invention. Heat tool 2, held securely in cradle 8, may be substantially mated to an extraction and capture apparatus comprised of a two-piece extraction chamber having substrate suspending screen 36, sequential Venturi-inducing tapered hot air intake 38, nozzle seating hip 68, lower extraction chamber 58, O-ring groove 92, high-temperature O-ring 60, and upper chamber 56. Upper chamber 56 houses a valve body 78 in valve housing 82 operated with a dual purpose substrate tamp and valve prop 86. Upper chamber 56 also houses tamp spacer 88 and tamp screen 90. Valve housing 82 comprises vapor ports 84 for allowing vapor to flow through from the two-piece extraction chamber to vapor collection balloon 76 when valve 78 is open. Vapor collection balloon 76 may be secured to two-piece extraction chamber using balloon securing O-ring 80, thereby allowing the two-piece extraction chamber to be in communication with vapor collection balloon 76.

Figure 10A:
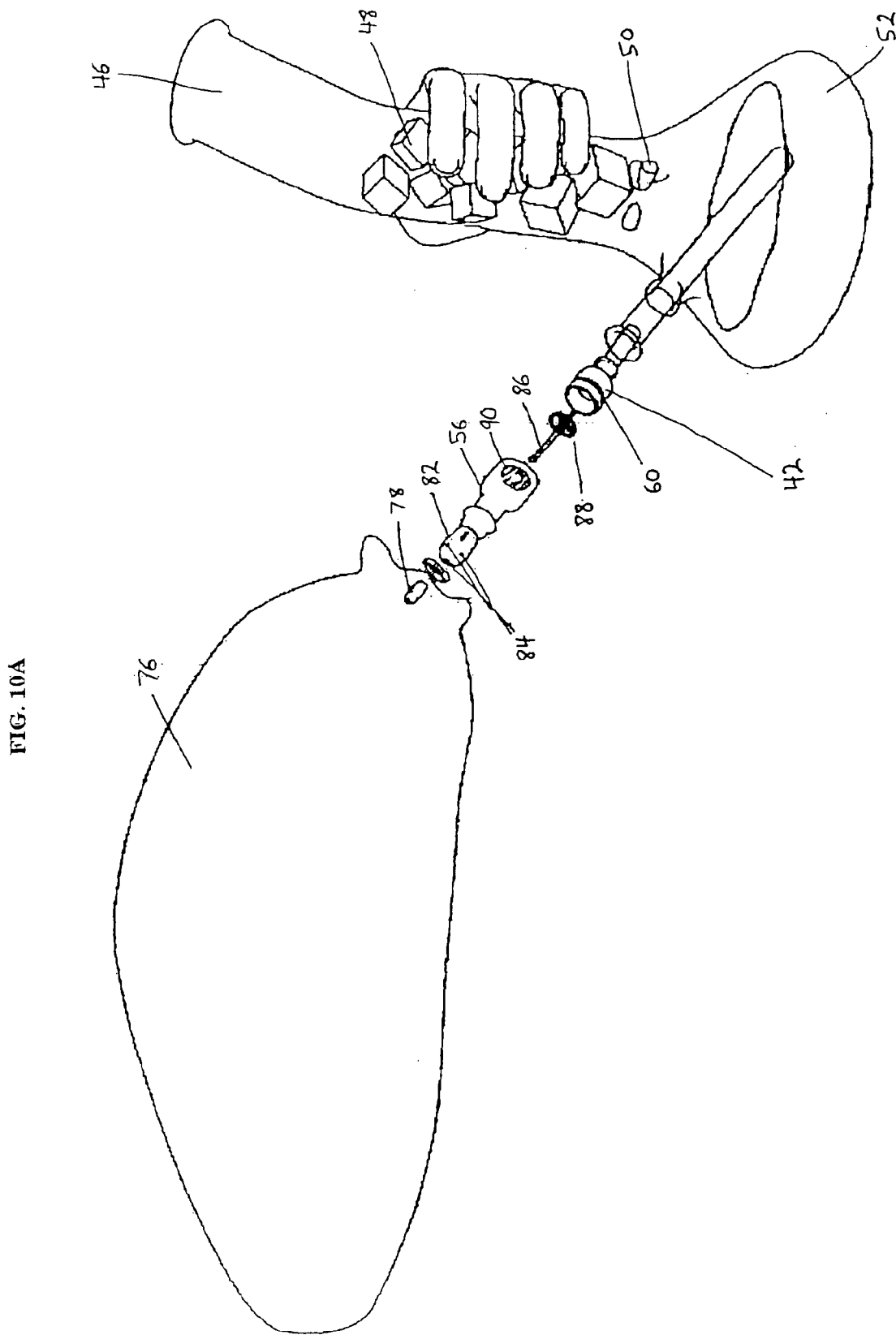
FIG. 10A is a partially separated orthographic cross-sectional view of the valve controlled vapor collection balloon to moisture conditioning vapor delivery vessel compatible configuration.
Figure 10B:
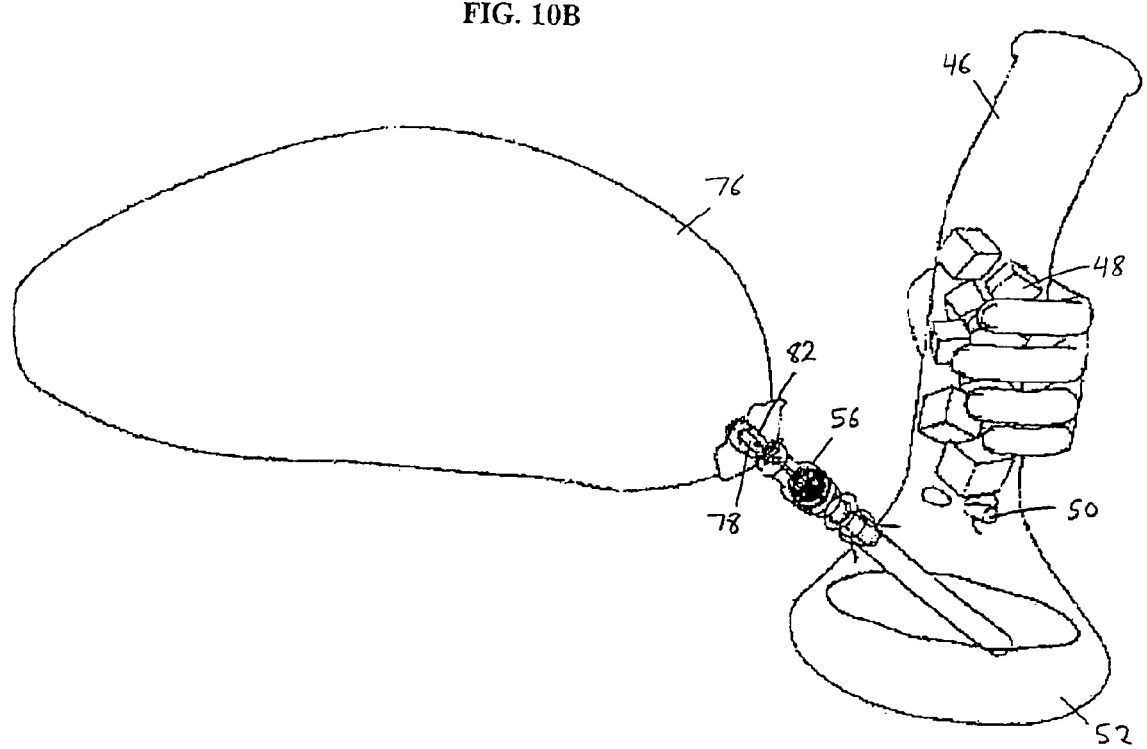
FIG. 10B is an assembled orthographic cross-sectional view of the valve controlled vapor collection balloon to moisture conditioning vapor delivery vessel compatible configuration.
Figure 10C:
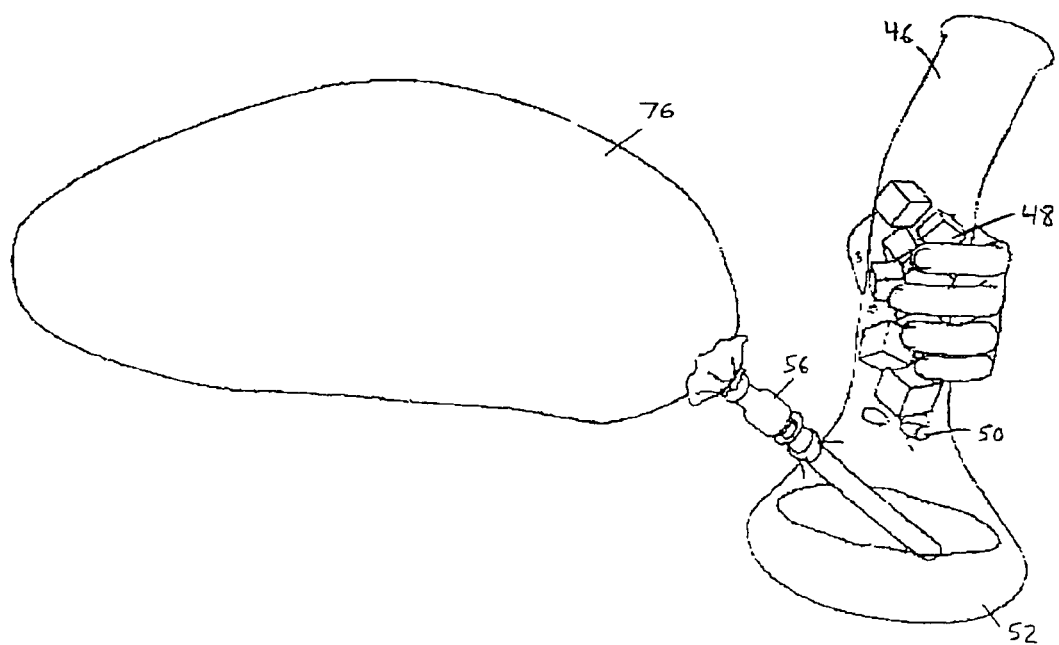
FIG. 10C is an assembled orthographic view of the valve controlled vapor collection balloon to moisture conditioning vapor delivery vessel compatible configuration.

FIGS. 10A through 10C illustrate the valve controlled vapor collection balloon to moisture conditioning vapor delivery vessel compatible configuration, representing the second of two basic steps in this method of one of the twelve configurations of the present invention. When vapor collection balloon 76 of FIGS. 9A-C is filled, it is detached from the intake and lower extraction chamber of FIGS. 9A-C with the valve housing 82 and upper chamber 56, and in turn mated to a delivery tube and valve prop for insertion into a moisture conditioning vapor delivery vessel 46, where the valve prop is positioned to open the valve body 78, and the liquid 52 acts as a secondary containment valve. Vapor collection balloon 76 may alternatively be mated to a vapor delivery tube for dry inhalations and gravity enabled user position controlled valve action.

Figure 11A:
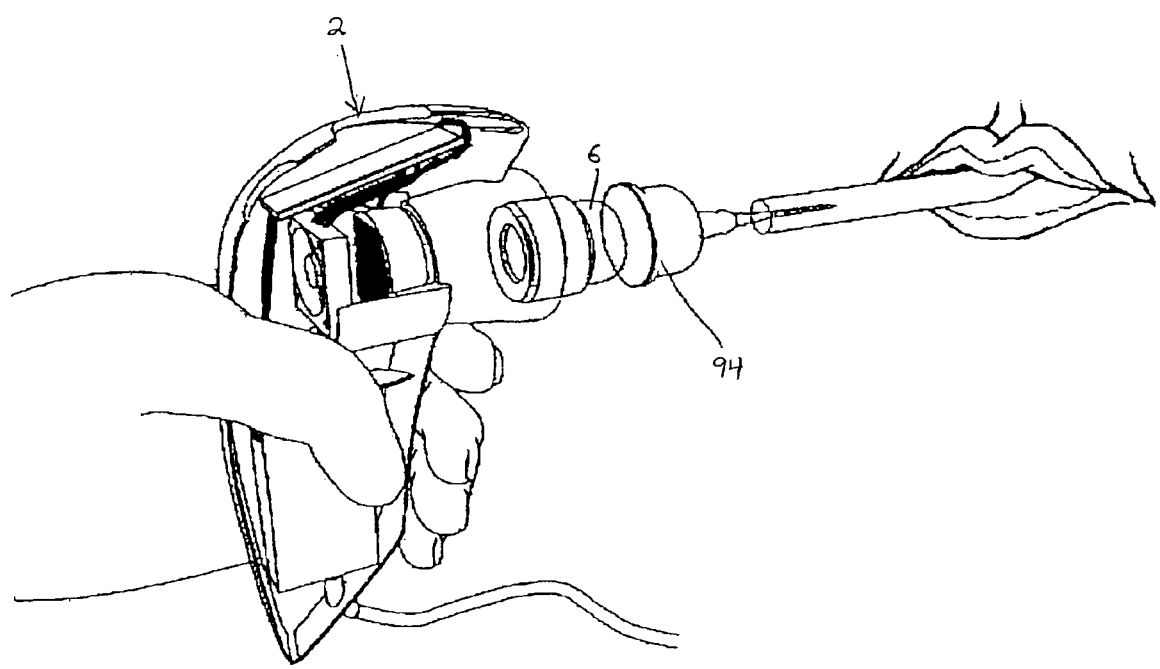
FIG. 11A is a partially separated orthographic cross-sectional view of the intra-convertible heat tool in hand operative, cigarette vapor extraction nozzle needle compatible mode.
Figure 11B:
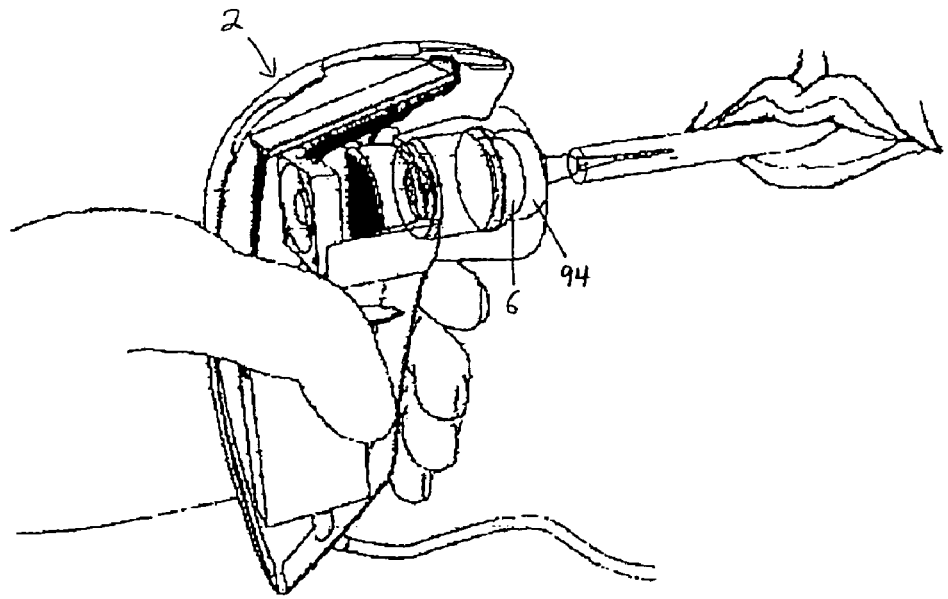
FIG. 11B is an assembled orthographic cross-sectional view of the intra-convertible heat tool in hand operative, cigarette vapor extraction nozzle needle compatible mode.
Figure 11C:
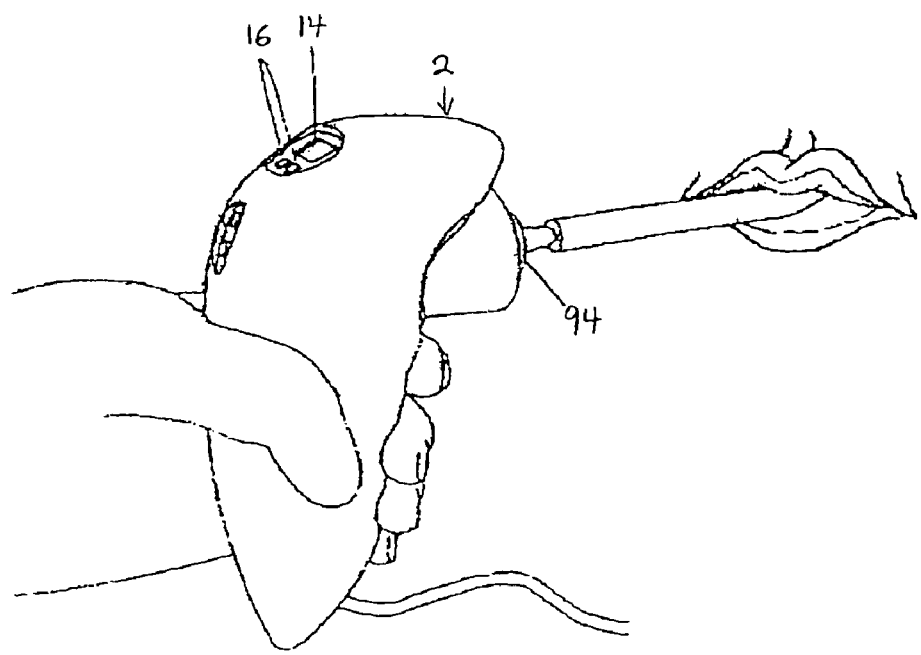
FIG. 11C is an assembled orthographic view of the intra-convertible heat tool in hand operative, cigarette vapor extraction nozzle needle compatible mode.

FIGS. 11A through 11C illustrate the intra-convertible heat tool 2 in hand operative, cigarette vapor extraction nozzle needle compatible mode, representing one of the twelve configurations of the present invention. Heat tool 2 may be substantially mated to cigarette needle nozzle adaptor 94, a nozzle attachment that tapers to a perforated needle-like shape for insertion into the open end of common cigarettes or cigars in order to enable vapor extraction from the rolled up tobacco or other plant substrate.

Figure 12A:
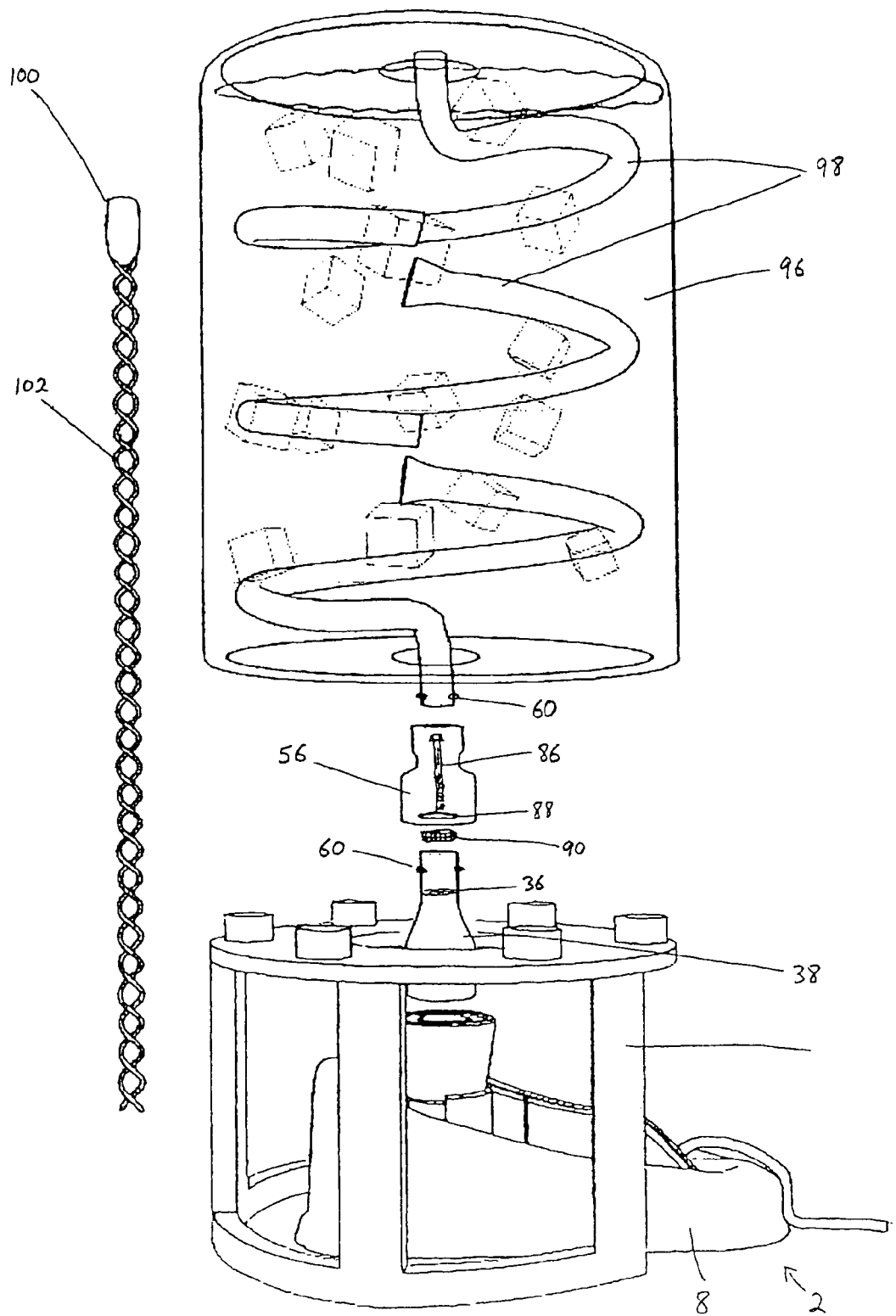
FIG. 12A is a partially separated orthographic cross-sectional view of the intra-convertible heat tool in cradle operative, vapor extraction chamber to ice water cooled vapor condensate collection coil assembly compatible mode.
Figure 12B:
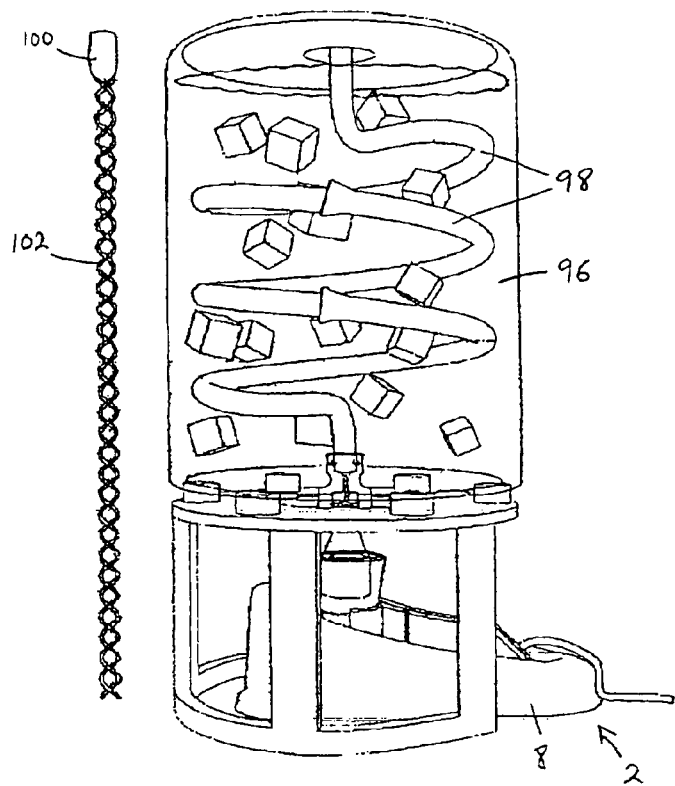
FIG. 12B is an assembled orthographic cross-sectional view of the intra-convertible heat tool in cradle operative, vapor extraction chamber to ice water cooled vapor condensate collection coil assembly compatible mode.
Figure 12C:
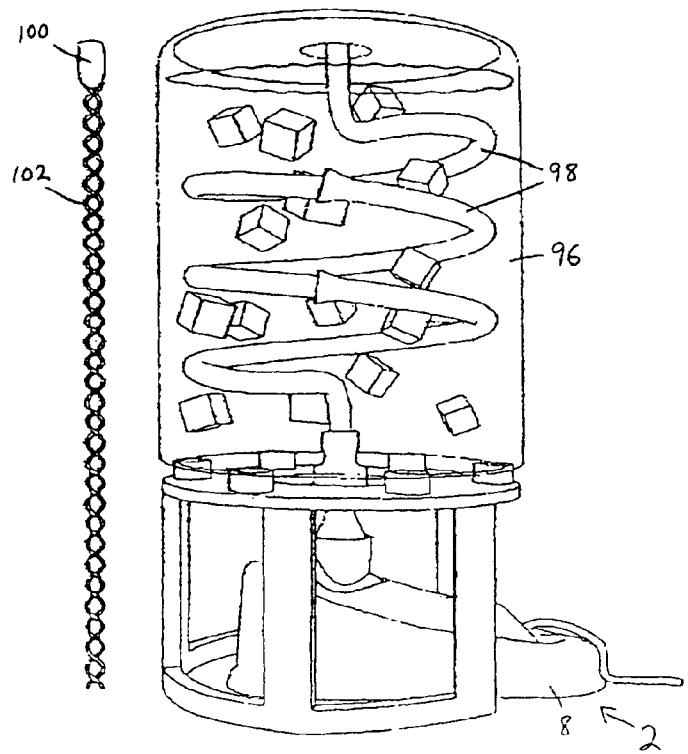
FIG. 12C is an assembled orthographic view of the intra-convertible heat tool in cradle operative, vapor extraction chamber to ice water cooled vapor condensate collection coil assembly compatible mode.

FIGS. 12A through 12C illustrate the intra-convertible heat tool 2 in cradle operative, vapor extraction chamber to ice water cooled vapor condensate collection coil assembly compatible mode, representing one of the twelve configurations of the present invention. Heat tool 2, held securely in cradle 8, may be substantially mated to an extraction chamber having a substrate suspending screen 36 and a sequential Venturi-inducing tapered hot air intake 38 and an upper chamber 56. Upper chamber 56 houses tamp screen 90, tamp spacer 88, and valve prop/tamp handle 86. The extraction chamber is substantially mated to a capture tube with modular cooling coils 98 housed within a container, such as ice water tank 96, for holding water and/or ice or other cooling substance in order to collect vapor condensates within the coils 98. This configuration may also comprise a flexible condensate collection tool handle 102 attached to condensate collection tip 100 for collecting vapor condensates within coils 98.

Figure 13A:
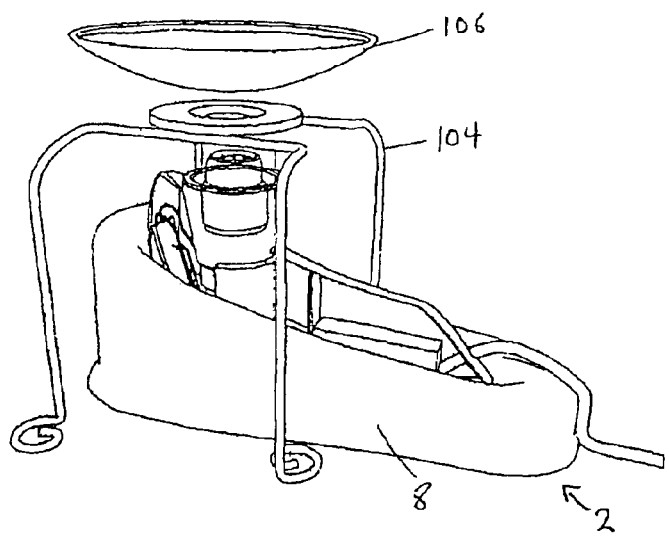
FIG. 13A is a partially separated orthographic cross-sectional view of the intra-convertible heat tool in cradle operative, aromatic water vapor diffuser compatible mode.
Figure 13B:
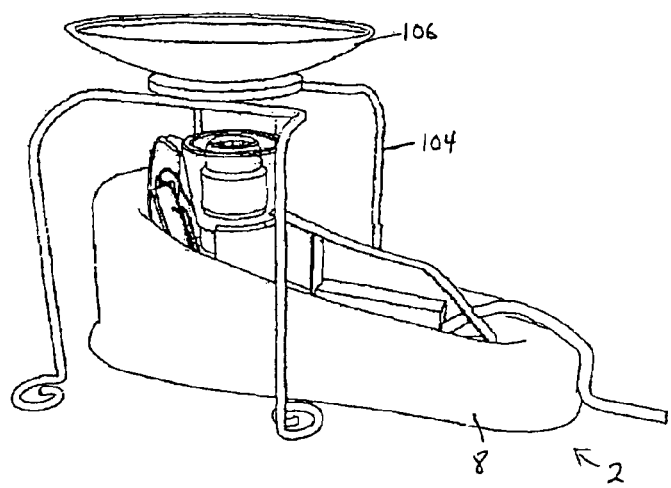
FIG. 13B is an assembled orthographic cross-sectional view of the intra-convertible heat tool in cradle operative, aromatic water vapor diffuser compatible mode.
Figure 13C:
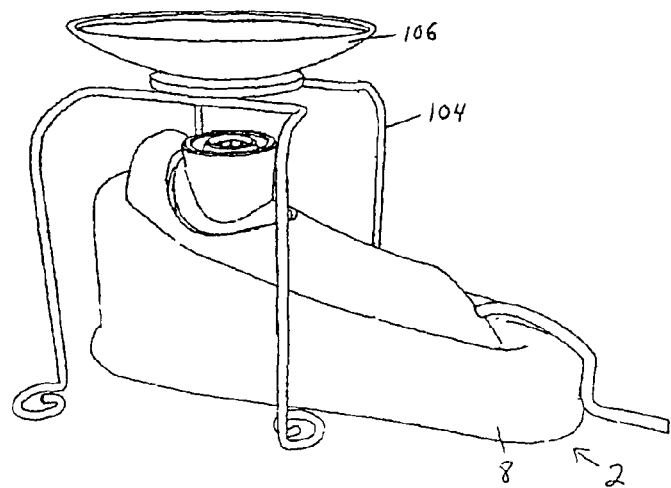
FIG. 13C is an assembled orthographic view of the intra-convertible heat tool in cradle operative, aromatic water vapor diffuser compatible mode.

FIGS. 13A through 13C illustrate the intra-convertible heat tool 2 in cradle operative, aromatic water vapor diffuser compatible mode, representing one of the twelve configurations of the present invention. Heat tool 2, held securely in cradle 8, may be unsubstantially mated to an open-air environmental diffuser assembly having an elevated assembly stand 104 and an elevated bowl shaped container of mixed water and oil, such as aromatic oil/water dish 106, that is heated in order to release aromatic vapors into the ambient surroundings for passive, rather than direct, inhalation.

Figure 14:
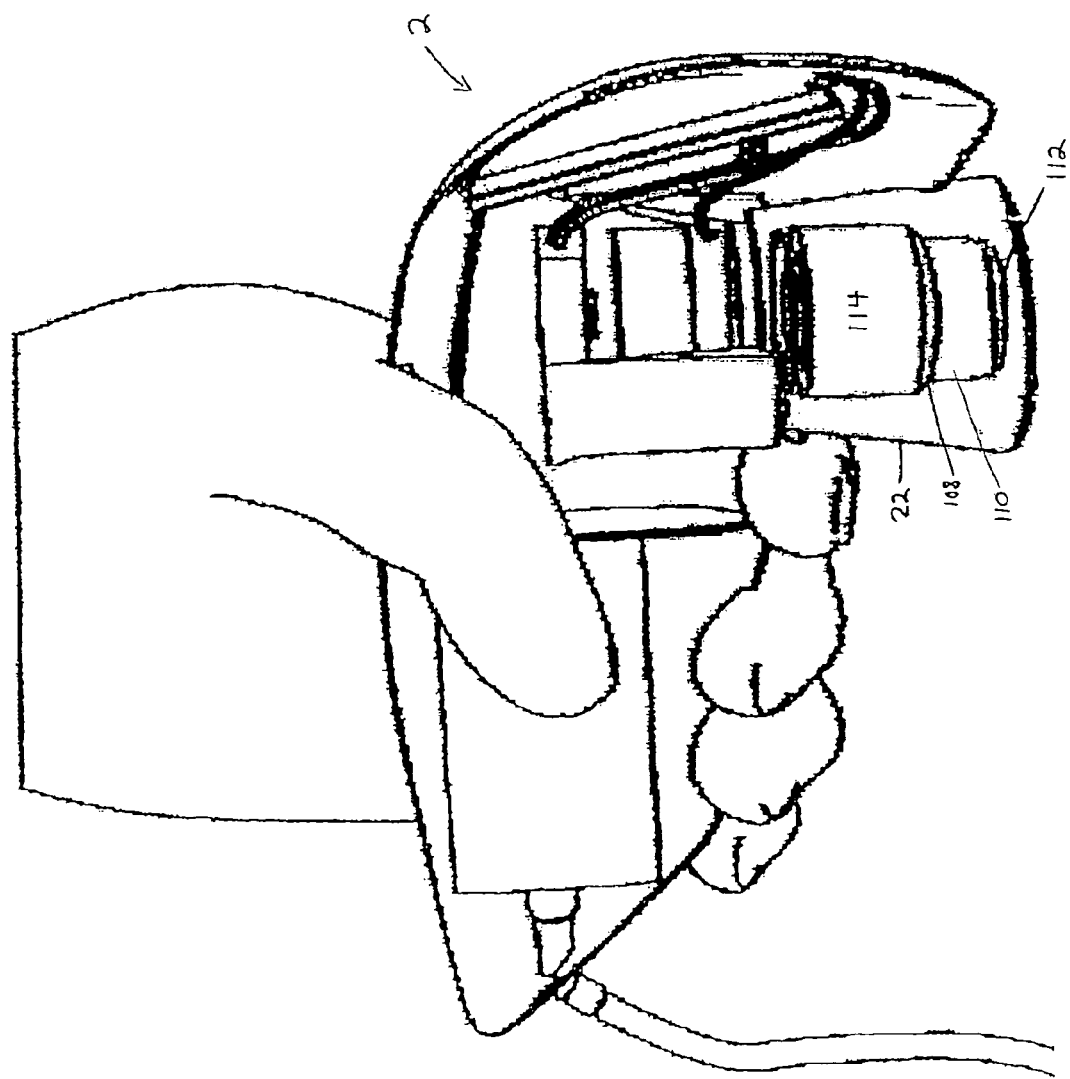
FIG. 14 is an enlarged orthographic cross-sectional view of the intra-convertible heat tool in hand operative mode.

FIG. 14 illustrates the intra-convertible nature of heating tool 2 and how it can accommodate conventional smoking pipe designs, cigarettes, and multiple compatible vapor extraction apparatuses. The hot air output of heating tool 2 flows through nozzle base 114 and diameter reduction step 108 to a tapered nozzle 110 with fixed vortical flow inducing bodies 7(FIG. 1A). Nozzle base 114 has a greater outer diameter than tapered nozzle 110, thereby creating diameter reduction step 108. In a preferred embodiment, the outer diameter of nozzle base 114 is about 1 and $5/16$ inches and the outer diameter of the tapered nozzle 110 (where it meets diameter reduction step 108 and nozzle base 114) is about 1 and $5/8$ inches. However, it is contemplated that the diameters may vary in size. The diameter reduction step 108 is the surface that bridges the difference between these two diameters. The size of the diameter reduction step 108 depends on whether or not the diameter reduction step 108 comprises a slope, and if so, the angle of the slope.

The ratio between the outer diameter of the tapered nozzle 110 and the outer diameter of the nozzle base 114 may be about $1:1 5/26$.

Diameter reduction step 108 may be designed to be substantially flat or level when tapered nozzle 110 is pointing straight up. Alternatively, diameter reduction step 108 may comprise a slope or grade. While tapered nozzle 110 is tapered, nozzle base 114 may either be tapered or have a consistent outer diameter. Extraction chambers and their adaptors may slide over tapered nozzle 110 and rest on diameter reduction step 108. In certain circumstances, The extraction chambers or their adaptors may slide over the diameter reduction step 108 as well, continuing on in between nozzle base 114 and nozzle sleeve 22.

The diameter reduction step 108 and tapered nozzle 110 accept interlocking nozzle attachments for adapted hand-held use with conventional smoking apparatuses (i.e. tobacco pipes or cigarettes). The diameter reduction step 108 and tapered nozzle 110 also accept an interchangeable and modular system of multiple vapor specific extraction chambers that feature a common intake seating design. Extraction chamber seating can occur dynamically, as the user holds heating tool 2 in his or her hand and directs tapered nozzle 110 into the extraction chamber intake. Seating can also occur statically, as the user simply places the extraction chamber on tapered nozzle 110 in a cradled position. Tapered nozzle 110 is recessed within nozzle sleeve 22 for safety purposes, as the nozzle end 112 will get hot with use. Experience with extraction systems using conventional thermo coupled hot air guns with exposed nozzles has indicated that such an exposed design is undesirable and potentially dangerous. The intake side of the extraction chamber sits on the lip of step 108 between nozzle 110 and nozzle sleeve 22 for a substantially air tight seal.

While the invention has been described with reference to an exemplary embodiment, it will be understood by those skilled in the art that various changes may be made and equivalents may be substituted for elements thereof without departing from the scope of the invention. In addition, many modifications and variations may be made to adapt a particular situation or material to the teachings without departing from the essential scope thereof. Such variations are likely to include, but should not be considered as limited to, various air flow valve assembly options, angles of intersection of the extraction chamber housings and heat intakes being compensatory to other angles, hot air flow output, and sources of sufficiently heated air flow other than the intra-convertible heat tool of the present invention's preferred form or a conventional heat gun.

Other variations are likely to include various extraction chamber intake or delivery tube bore altering rifling intended to create air flow turbulence within the chambers, and external handles for ease of handling. The present invention may also include non-distally offset intakes for both one-piece dry (or moisture) systems and two-piece dry (or moisture) systems. Additionally, an oxidation valve may be added to delivery vessels to enable controlled dilution ratio of air to vapor.

The present invention may comprise a thermo-coupled controlled, continuously variable hot air gun (medical or non-medical grade) or other hot air sources (medical or non-medical grade). It may also comprise turbulence creating members (i.e. turbines, rifling, etc.) within the intakes and/or extraction chambers. Cooling coils or fins may be present on the outside of delivery tubes. A tightly woven stainless steel coil in the shape of a disk may sit on top of or be used in lieu of the substrate supporting screen in any of the extraction chambers to enable a combination convective/conductive extraction for oils, fluids, or powder concentrates. Additionally, a mass of small glass, ceramic, or metal balls may sit on top of or be used in lieu of the substrate supporting screen in any of the extraction chambers to enable a combination convective/conductive extraction for oils, fluids, or powder concentrates.

Therefore, it is intended that the invention not be limited to the particular embodiment disclosed as the best mode contemplated for carrying out this invention.

What is claimed is:

1. A thermal vapor extraction and delivery system comprising:
   an elongated body, a portion of which comprises a handle having a gripping surface ergonomically shaped to fit within the grasp of a human hand;
   a heating element disposed within the casing;
   an output nozzle coupled to the casing and extending radially from the elongated body at a position above the handle, the output nozzle extending from a nozzle base to a nozzle output end; the nozzle base having a greater outer diameter than the nozzle output end and forming a step at a transition between the nozzle base and the nozzle output end;
   a nozzle sleeve spaced apart from and surrounding the output nozzle, the nozzle sleeve extending no further than the than the nozzle output end;
   a fan positioned substantially behind the heating element so as to blow ambient air through the heating element, the output nozzle base and out through the nozzle output end;
   a cradle having a substantially planar bottom surface and a substantially concave top surface configured to mate with and securely hold the elongated body in a horizontal position such that the nozzle output end points upward;
   a thermal control circuit coupled to the heater to maintain the heating element at a desired temperature.

2. The system of claim 1 wherein the body is formed from a high-temperature resistant plastic.

3. The system of claim 1 wherein the body further comprises ambient air intakes in communication with the fan.

4. The system of claim 1 wherein the body further comprises power, temperature and fan controls.

5. The system of claim 1 wherein the body further comprises a battery.

6. The system of claim 1 wherein the body further comprises a power converter.

7. The system of claim 1 wherein the casing, the heating element, the fan, the output nozzle, and said nozzle sleeve are all formed from medical grade materials.

8. The system of claim 1 wherein the output nozzle is formed from ceramic material.

9. The system of claim 1 wherein the output nozzle is configured to mate with a tapered nozzle attachment, and in thermal communication with a bowl on a standard smoking pipe design.

10. The system of claim 1 wherein the output nozzle is configured to mate with a one-piece extraction chamber, the one-piece extraction chamber having a substrate suspending screen, sequential Venturi-inducing tapered intake and a lower chamber that is compatible with conventional dry smoking pipe delivery structures and vapor specific dry delivery structures.

11. The system of claim 1 wherein the output nozzle is configured to mate with a one-piece extraction chamber having a substrate suspending screen, a sequential Venturi-inducing tapered intake and a lower chamber that is compatible with conventional moisture conditioning smoking pipe designs and vapor specific moisture conditioning delivery vessels.

12. The system of claim 1 wherein the output nozzle is configured to mate with a two-piece extraction chamber having a substrate suspending screen, a sequential Venturi-inducing tapered intake and a lower chamber that is compatible with conventional dry smoking pipe designs and vapor specific dry delivery structures.

13. The system of claim 1 wherein the output nozzle is configured to mate with a two-piece extraction chamber having a substrate suspending screen, a sequential Venturi-inducing tapered intake and a lower chamber that is compatible with conventional moisture conditioning smoking pipe designs and vapor specific moisture conditioning delivery vessels.

14. The system of claim 1 wherein the output nozzle is configured to mate with a two-piece extraction chamber having a substrate suspending screen, a sequential Venturi-inducing tapered intake and an upper chamber coupled to a vapor delivery hose, the vapor delivery hose is connected to a mouthpiece.

15. The system of claim 1 wherein the output nozzle is configured to mate with a two-piece extraction chamber having a substrate suspending screen, a sequential Venturi-inducing tapered intake and an upper chamber coupled to a vapor delivery hose, the vapor delivery hose is connected to a moisture conditioning vapor delivery vessel.

16. The system of claim 1 wherein:
the output nozzle is configured to mate with an extraction and capture apparatus, the extraction and capture apparatus comprising a two piece extraction chamber having a substrate suspending screen, a sequential Venturi-inducing tapered intake and an upper chamber; and
the upper chamber houses a valve operated with a dual purpose substrate tamp and a valve prop, and is in communication with a vapor capture balloon.

17. The system of claim 1 wherein the output nozzle is configured to mate with a nozzle attachment that tapers to a perforated needle-like shape for insertion into the open end of common cigarettes or cigars, enabling vapor extraction.

18. The system of claim 1 wherein the output nozzle is configured to mate with an extraction chamber having a substrate suspending screen, a sequential Venturi-inducing tapered intake and an upper chamber, said upper chamber is substantially mated to a capture tube with modular cooling coils housed within a container for holding cooling substance, wherein vapor condensates may be collected within said modular cooling coils.

* * * * *